(12) United States Patent
Ueda

(10) Patent No.: US 10,682,473 B2
(45) Date of Patent: Jun. 16, 2020

(54) MEDICAL PUNCTURE NEEDLE AND METHOD FOR MANUFACTURING PUNCTURE NEEDLE

(71) Applicant: TERUMO KABUSHIKI KAISHA, Tokyo (JP)

(72) Inventor: Takehiko Ueda, Yamanashi (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 285 days.

(21) Appl. No.: 15/470,781

(22) Filed: Mar. 27, 2017

(65) Prior Publication Data

US 2017/0274153 A1 Sep. 28, 2017

(30) Foreign Application Priority Data

Mar. 28, 2016 (JP) .................. 2016-063633

(51) Int. Cl.
*A61M 5/32* (2006.01)
*A61B 5/15* (2006.01)
*A61B 5/153* (2006.01)
*B21G 1/08* (2006.01)
(Continued)

(52) U.S. Cl.
CPC ....... *A61M 5/3286* (2013.01); *A61B 5/15003* (2013.01); *A61B 5/153* (2013.01); *A61B 5/150282* (2013.01); *A61B 5/150396* (2013.01); *B21G 1/08* (2013.01); *A61M 5/158* (2013.01); *B21G 1/12* (2013.01)

(58) Field of Classification Search
CPC .......... A61M 5/3286; A61M 2205/195; A61B 5/150396
See application file for complete search history.

(56) References Cited

U.S. PATENT DOCUMENTS 2,697,438 A 12/1954 Hickey et al.
3,071,135 A * 1/1963 Baldwin ............. A61M 5/3286
604/274
(Continued)

FOREIGN PATENT DOCUMENTS

FR 2481930 A1 11/1981
GB 0 904 291 A 8/1962
(Continued)

OTHER PUBLICATIONS

Extended European Search Report issued in the corresponding EP Patent Application Ser. No. 17773616.2, dated Jul. 26, 2019.

*Primary Examiner* — William R Carpenter
(74) *Attorney, Agent, or Firm* — Foley & Lardner LLP

(57) ABSTRACT

A medical puncture needle includes a rod-shaped main body portion; and a blade surface formed at a distal end portion of the main body portion. The blade surface includes a first blade surface portion and a second blade surface portion that intersect to form a blade edge. A needle tip is formed at a location at which a distal end of the blade edge intersects a first ridge line at an outer edge of the first blade surface and a second ridge line at an outer edge of the second blade surface. At least one of the blade surface portions is planar, and, in a central axis direction of the main body portion, said at least one blade surface portion extends to a location proximal of a middle position of a blade surface region in which the blade surface is formed.

5 Claims, 22 Drawing Sheets

(51) Int. Cl.
*A61M 5/158* (2006.01)
*B21G 1/12* (2006.01)

(56) References Cited

U.S. PATENT DOCUMENTS

| | | | | |
|---|---|---|---|---|
| 3,308,822 | A * | 3/1967 | De Luca | A61M 5/3286 |
| | | | | 604/274 |
| 5,575,780 | A * | 11/1996 | Saito | A61M 5/3286 |
| | | | | 604/264 |
| 5,752,942 | A * | 5/1998 | Doyle | B24B 19/16 |
| | | | | 604/274 |
| 6,517,523 | B1 * | 2/2003 | Kaneko | A61M 5/3286 |
| | | | | 163/5 |
| 9,050,169 | B2 * | 6/2015 | Schieber | A61F 9/00781 |
| 2004/0111066 | A1 * | 6/2004 | Prais | B24B 19/16 |
| | | | | 604/239 |
| 2005/0107751 | A1 * | 5/2005 | Yatabe | A61M 5/158 |
| | | | | 604/272 |
| 2013/0218102 | A1 * | 8/2013 | Iwase | A61M 5/42 |
| | | | | 604/272 |

FOREIGN PATENT DOCUMENTS

| | | | | |
|---|---|---|---|---|
| JP | 10-057490 | A | 3/1998 | |
| JP | 2000-262615 | A | 9/2000 | |
| JP | 2003-290354 | A | 10/2003 | |
| JP | 2006-280503 | A | 10/2006 | |
| WO | WO-2008132660 | A1 * | 11/2008 | A61M 5/3286 |
| WO | WO-2012/073947 | A1 | 6/2012 | |
| WO | WO-2015/114706 | A1 | 8/2015 | |
| WO | WO-2015114706 | A1 * | 8/2015 | B21G 1/08 |
| WO | WO-2016132577 | A1 * | 8/2016 | A61B 8/12 |
| WO | WO-2017017934 | A1 * | 2/2017 | A61M 5/32 |

* cited by examiner

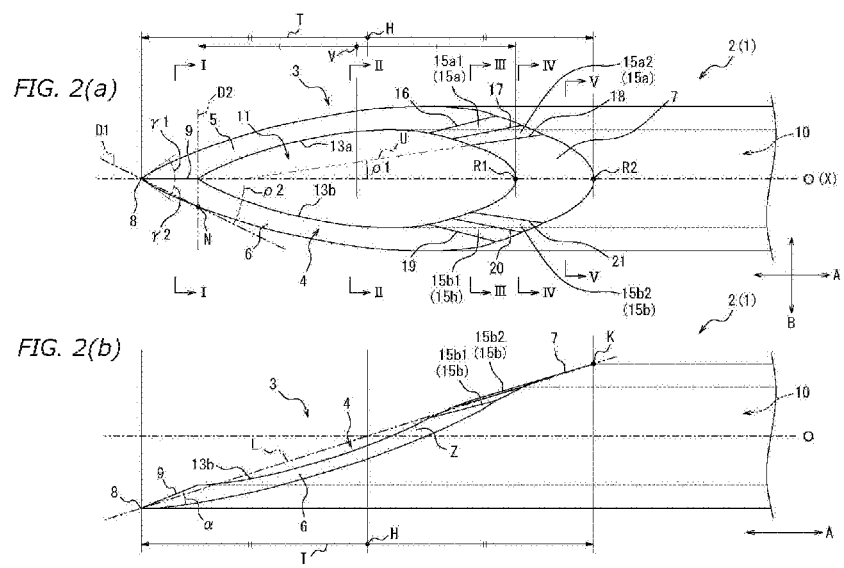

I-I CROSS-SECTION

II-II CROSS-SECTION

III-III CROSS-SECTION

IV-IV CROSS-SECTION

V-V CROSS-SECTION

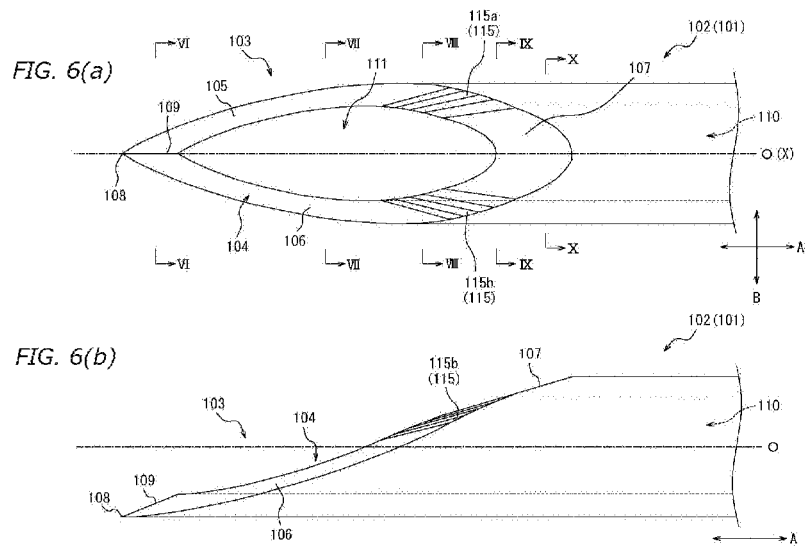

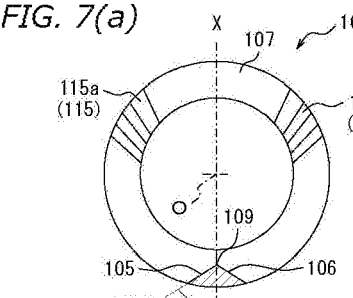
FIG. 7(a) VI-VI CROSS-SECTION
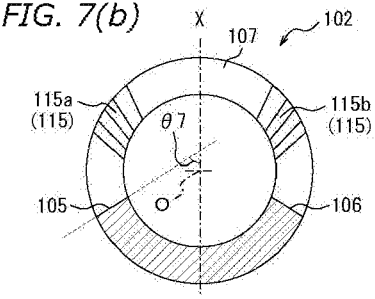
FIG. 7(b) VII-VII CROSS-SECTION
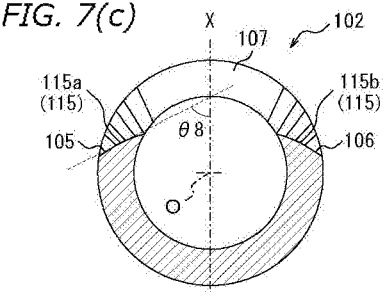
FIG. 7(c) VIII-VIII CROSS-SECTION
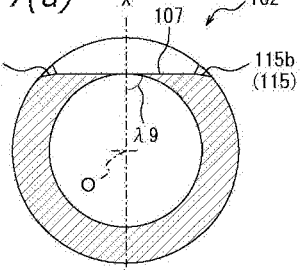
FIG. 7(d) IX-IX CROSS-SECTION
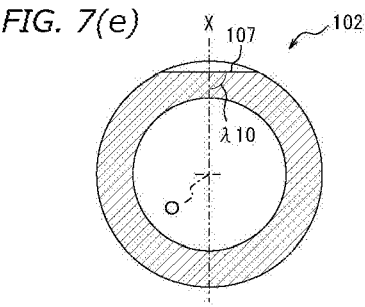
FIG. 7(e) X-X CROSS-SECTION

XI-XI CROSS-SECTION

XII-XII CROSS-SECTION

XIII-XIII CROSS-SECTION

XIV-XIV CROSS-SECTION

XV-XV CROSS-SECTION

XVI-XVI CROSS-SECTION

XVII-XVII CROSS-SECTION

XVIII-XVIII CROSS-SECTION

XIX-XIX CROSS-SECTION

XX-XX CROSS-SECTION

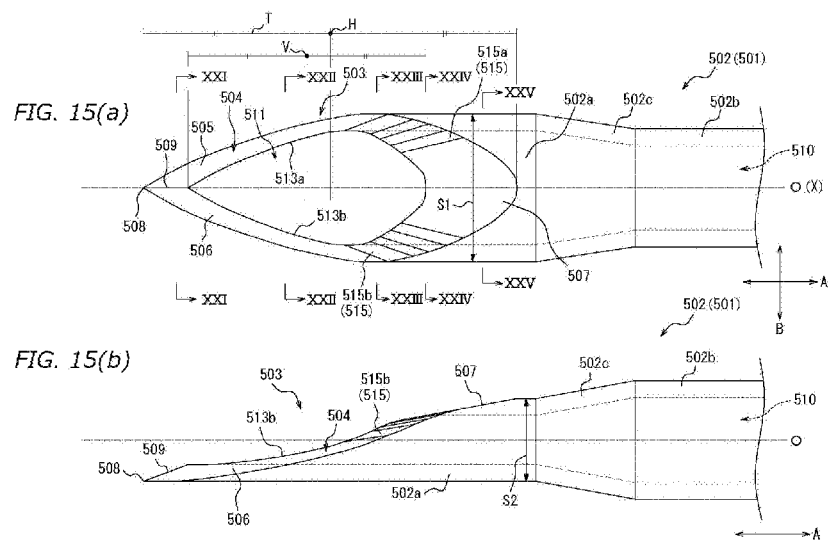

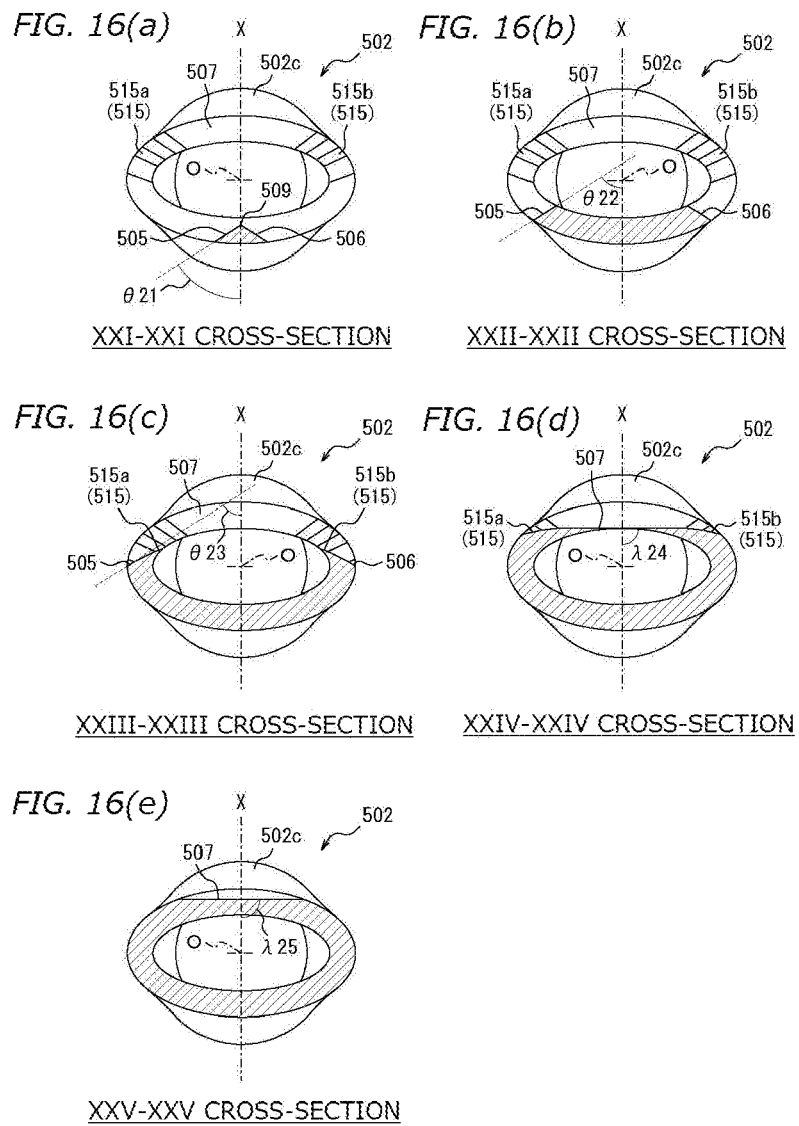

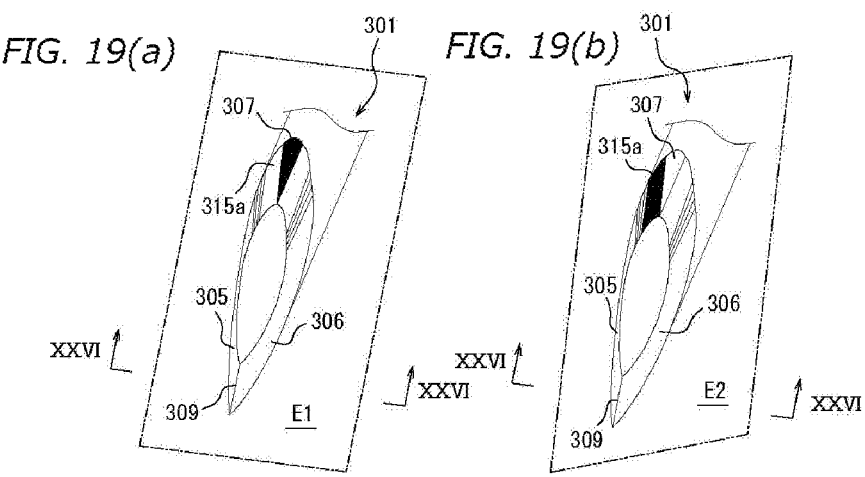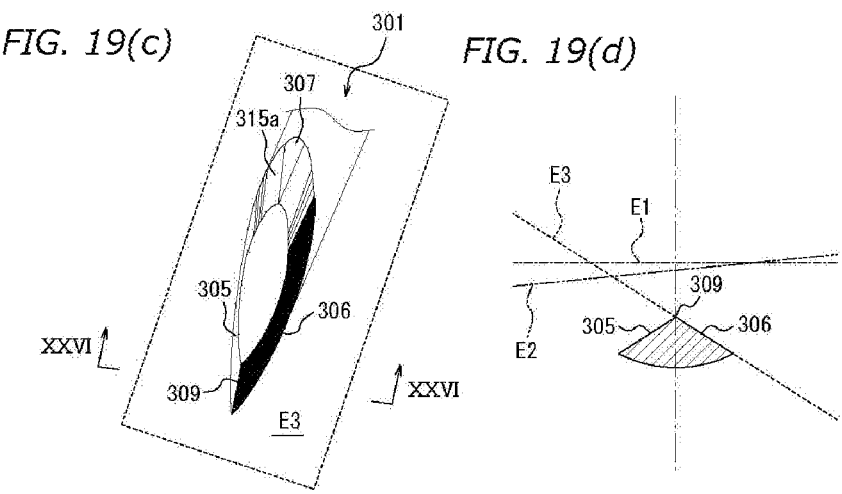

XXVII-XXVII CROSS-SECTION

XXVIII-XXVIII CROSS-SECTION

XXIX-XXIX CROSS-SECTION

XXX-XXX CROSS-SECTION

XXXI-XXXI CROSS-SECTION

MEDICAL PUNCTURE NEEDLE AND METHOD FOR MANUFACTURING PUNCTURE NEEDLE

CROSS-REFERENCE TO RELATED APPLICATION

The present application claims priority to Japanese Application No. 2016-063633, filed on Mar. 28, 2016, which is hereby incorporated by reference in its entirety.

BACKGROUND

The present disclosure relates to a medical puncture needle and a method for manufacturing a puncture needle.

Conventionally, as a medical puncture needle such as a blood sampling needle or an indwelling needle for infusion, in order to reduce pain when puncturing the puncture needle to a human body, a needle equipped with a distal end portion having a plurality of blade surfaces having different angles with respect to a longitudinal direction of the puncture needle has been known.

JP 2000-262615 A discloses an injection needle as such a puncture needle. The injection needle of JP 2000-262615 A is an injection needle in which a pointed end portion of a cylindrical main body is obliquely cut from one side to form a tapered pointed end portion, and includes a first inclined surface that is connected from an outer periphery of the cylindrical main body and is formed at a predetermined angle with respect to an axis direction (longitudinal direction) of the main body, a second inclined surface that is connected to the first inclined surface and is formed at an angle with respect to the axis direction of the main body larger than that of the first inclined surface, and a third inclined surface that is connected to the second inclined surface, connected to the blade tip and is formed at an angle with respect to the axis direction of the main body larger than that of the second inclined surface.

Further, JP 10-57490 A also discloses a hypodermic injection needle as a puncture needle. The hypodermic injection needle of JP 10-57490 A has a distal end having a shape of a polygonal angular surface, and the distal end having the shape of the polygonal angle surface has a main inclined angle surface, a pair of intermediate inclined angle surfaces, and a pair of distal end inclined angle surfaces.

SUMMARY

As in the injection needles of JP 2000-262615 A and JP 10-57490 A, by using a distal end portion having a blade surface to which a plurality of surfaces having different angles with respect to the longitudinal direction is connected, it is possible to reduce the piercing resistance caused by a ridge line (junction) formed at a boundary between the surfaces and to alleviate the pain when puncturing the injection needle into the human body.

In the case of a puncture needle punctured into a vessel such as a blood vessel, it is common to use a puncture needle having a short blade surface length in the direction of the central axis of the puncture needle so that the entire blade surface can easily enter the vessel. With such a puncture needle having a short blade surface length in the central axis direction, even if a plurality of surfaces having different angles with respect to the longitudinal direction is formed to provide the multi-sided blade surfaces, it is not possible to reduce an angle (hereinafter referred to as "blade tip angle") formed by the blade tips of the blade surfaces in a side view, and the blade tip angle tends to become relatively large. Therefore, there is a problem that the piercing resistance of the blade tip increases and it is difficult to alleviate the pain at the time of piercing of the blade tip. Also, if the piercing resistance of the blade tip is high, it is not possible to smoothly pierce the vessel wall such as a blood vessel wall when puncturing the vessel, and the vessel may be pushed by the blade tip to escape.

An object of the present disclosure is to provide a medical puncture needle having a blade surface shape capable of reducing the blade tip angle irrespective of the length of the blade surface, and a method for manufacturing the medical puncture needle.

In a medical puncture needle of a first embodiment of the present invention, a blade surface is formed at a distal end portion of a rod-shaped main body portion, and the blade surface includes a first blade surface portion and a second blade surface portion which form a blade edge having a needle tip as one end by ridge lines intersecting with each other on a distal end side, and at least one blade surface portion of the first blade surface portion and the second blade surface portion is made up of a plane, and the at least one blade surface portion extends to be closer to a proximal end side of the main body portion than a middle position in a central axis direction of the main body portion of a blade surface region in which the blade surface is formed.

In one aspect, the blade surface includes a third blade surface portion which is continuous with the at least one blade surface portion via at least one connecting blade surface portion and is made up of a plane or a curved surface constituting a proximal end of the blade surface.

In one aspect, the at least one connecting blade surface portion includes a planar blade surface portion made up of a plane.

In one aspect, the at least one connecting blade surface portion includes a plurality of planar blade surface portions formed continuously.

In one aspect, the at least one connecting blade surface portion includes a curved blade surface portion made up of a curved surface.

In one aspect, a ridge portion formed by a ridge line in which the third blade surface portion and the at least one connecting blade surface portion intersect with each other extends along the central axis line.

In one aspect, the main body portion defines a hollow portion which has a distal end opening defined by an inner edge of the blade surface as one end, and one end on the proximal end side of the main body portion in the ridge portion is located between one end on the proximal end side of the main body portion at the inner edge of the blade surface and the proximal end of the blade surface, in the central axis direction.

In one aspect, a straight line passing through the needle tip and the proximal end of the blade surface in a side view in which the needle tip is located at one end in a direction orthogonal to the central axis direction is inclined with respect to the central axis line at an angle of 13 degrees or more and 20 degrees or less.

In one aspect, each of the first blade surface portion and the second blade surface portion is made up of a plane, and the first blade surface portion and the second blade surface portion extend to be closer to the proximal end side of the main body portion than the middle position of the blade surface region.

In another embodiment of the present invention, a method for manufacturing a medical puncture needle which forms a blade surface at one end portion of a tubular member, the method including: forming an original shape blade surface portion inclined with respect to a central axis direction of the tubular member; and forming a first blade surface portion and a second blade surface portion which form a blade edge having a needle tip as one end by ridge lines intersecting with each other, from a part of a distal end side of the original shape blade surface portion, and at least one blade surface portion of the first blade surface portion and the second blade surface portion is formed by a plane which extends to be closer to other end portion side of the tubular member than a middle position in the central axis direction of the original shape blade surface region in which the original shape blade surface portion is formed.

In one aspect, the method for manufacturing a medical puncture needle, further includes: forming at least one connecting blade surface portion which connects a third blade surface portion made up of a part of the original shape blade surface portion and the at least one blade surface portion, and, when forming the at least one connecting blade surface portion, a ridge portion formed by a ridge line in which the third blade surface portion and the at least one connecting blade surface portion intersect with each other extends along the central axis line, and one end on the other end portion side of the tubular member in the ridge portion is formed to be located between one end on the other end portion side of the tubular member at the inner edge of the original shape blade surface portion and one end on the other end portion side of the tubular member in the original shape blade surface portion, in the central axis direction.

In a medical puncture needle of another embodiment of the present invention, a blade surface is formed in a distal end portion of a tubular main body portion, and an inner edge of the blade surface includes a curved portion which extends to be curved in a concave shape from one end on a needle tip side of the inner edge, in a side view in which the needle tip is located at one end in a direction orthogonal to a central axis direction of the main body portion, and the curved portion extends to be closer to a proximal end side of the main body portion than a middle position of the inner edge in the central axis direction.

According to certain embodiments of the present invention, it is possible to provide a medical puncture needle having a blade surface shape capable of reducing the blade tip angle irrespective of the length of the blade surface, and a method for manufacturing the medical puncture needle.

BRIEF DESCRIPTION OF THE DRAWINGS

FIGS. 2(a) and 2(b) are enlarged views of the vicinity of a distal end portion of a main body portion of the puncture needle illustrated in FIGS. 1(a) and 1(b), respectively.

FIGS. 6(a) and 6(b) are enlarged views of the vicinity of the distal end portion of the main body portion of the puncture needle illustrated in FIGS. 5(a) and 5(b), respectively.

FIGS. 7(a), 7(b), 7(c), 7(d) and 7(e) are cross-sectional views taken along a line VI-VI, a line VII-VII, a line VIII-VIII a line IX-IX and a line X-X in FIG. 6(a), respectively.

FIGS. 15(a) and 15(b) are enlarged views of the vicinity of the distal end portion of the main body portion of the puncture needle illustrated in FIGS. 14(a) and 14(b), respectively.

FIGS. 16(a), 16(b), 16(c), 16(d) and 16(e) are cross-sectional views taken along a line XXI-XXI, a line XXII-XXII, a line XXIII-XIII, a line XXIV-XXIV, and a line XXV-XXV of FIG. 15(a), respectively.

FIGS. 19(a), 19(b), and 19(c) illustrate a first virtual plane including a third blade surface portion of the puncture needle illustrated in FIGS. 10(a) and 10(b), a second virtual plane including a first connection blade surface portion, and a third virtual plane including a second blade surface portion, and FIG. 19(d) is a view illustrating a relation among three virtual planes in the XXVI-XXVI cross-section in FIGS. 19(a) to 19(c).

DETAILED DESCRIPTION

Figure 1A:
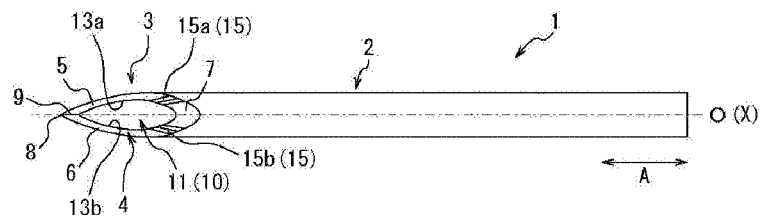
FIGS. 1(a), 1(b), 1(c) and 1(d) area plan view and a side view of a front side of a puncture needle 1, and a plan view and a perspective view of a back side thereof, as an embodiment of the present invention, respectively.

Hereinafter, a medical puncture needle and a method for manufacturing a medical puncture needle according to several embodiments the present invention will be described with reference to FIGS. 1(a) to 22(e). In each drawing, common members are denoted by the same reference numerals.

First Embodiment

Figure 1B:
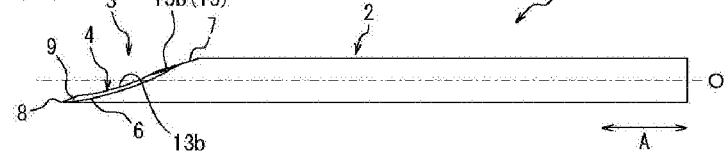
Figure 1C:
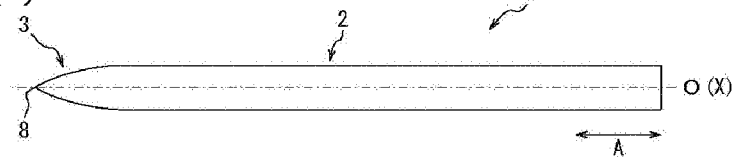
Figure 1D:
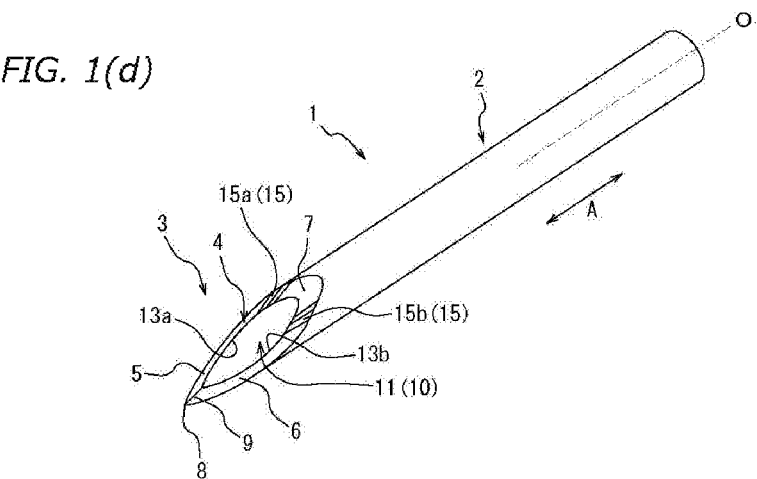

First, a puncture needle 1 as an embodiment of a medical puncture needle according to the present invention will be described. FIGS. 1(a) to 1(d) are views illustrating a puncture needle 1. Specifically, FIG. 1(a) is a plan view of a front side of the puncture needle 1, FIG. 1(b) is a side view of the puncture needle 1, and FIG. 1(c) is a plan view of a back side of the puncture needle 1. FIG. 1(d) is a perspective view of the puncture needle 1. Further, FIGS. 2(a) and 2(b) are enlarged views of the vicinity of a distal end portion 3 of a main body portion 2 of the puncture needle 1 illustrated in FIGS. 1(a) and 1(b), respectively.

As illustrated in FIGS. 1(a) to 1(d), 2(a) and 2(b), the puncture needle 1 is provided with a rod-shaped main body portion 2, and a blade surface 4 is formed at the distal end portion 3 of the main body portion 2. The main body portion 2 defines a hollow portion 10 that communicates in an axis direction (hereinafter, referred to as "central axis direction A") parallel to a central axis O of the main body portion 2.

The main body portion 2 is a tube body having a hollow rod shape, that is, a tubular shape. More specifically, the main body portion 2 of the present embodiment is a tube body having a substantially circular sectional outer shape. Here, the "section" of the "sectional outer shape" means a cross-section that is orthogonal to the central axis O of the main body portion 2.

The blade surface 4 is made up of a plurality of blade surface portions, and as illustrated in FIGS. 1(a) to 1(d), 2(a) and 2(b), the blade surface 4 of the present embodiment includes a first blade surface portion 5 made up of a single plane, a second blade surface portion 6 made up of a single plane, a third blade surface portion 7 made up of a single plane, and a plurality of connecting blade surface portions 15 which connects the first blade surface portion 5, the second blade surface portion 6 and the third blade surface portion 7. Each of the connecting blade surface portions 15 of the present embodiment is made up of a single plane. Further, the plurality of connecting blade surface portions 15 of the present embodiment includes a first connecting blade surface portion 15a which connects the first blade surface portion 5 and the third blade surface portion 7, and a second connecting blade surface portion 15b which connects the second blade surface portion 6 and the third blade surface portion 7.

The first blade surface portion 5 and the second blade surface portion 6 are formed on the distal end side of the main body portion 2 in the blade surface 4. Further, the first blade surface portion 5 and the second blade surface portion 6 form a blade edge 9 with a needle tip 8 as one end by ridge lines which intersect with each other. The "needle tip" means the distal end of the puncture needle 1 in the central axis direction A, that is, the distal end of the main body portion 2, and also means a blade tip which is the distal end of the blade surface 4. Therefore, hereinafter, a "distal end side" means a needle tip side in the central axis direction A, and a "proximal end side" means a side opposite to the needle tip side in the central axis direction A.

The first blade surface portion 5 is continuous with the first connecting blade surface portion 15a on the proximal end side of the main body portion 2. The second blade surface portion 6 is continuous with the second connecting blade surface portion 15b on the proximal end side of the main body portion 2.

The third blade surface portion 7 is formed on the proximal end side of the main body portion 2 of the blade surface 4 and constitutes the proximal end of the blade surface 4. Specifically, the third blade surface portion 7 is continuous with the tubular outer circumferential surface of the main body portion 2 on the proximal end side of the main body portion 2. Further, the third blade surface portion 7 is continuous with the connecting blade surface portion 15 on the distal end side of the main body portion 2. More specifically, the third blade surface portion 7 is connected to the first connecting blade surface portion 15a and the second connecting blade surface portion 15b on the distal end side of the main body portion 2.

The plurality of connecting blade surface portions 15 has a plurality of first connecting blade surface portions 15a and a plurality of second connecting blade surface portions 15b. Specifically, the number of the plurality of connecting blade surface portions 15 in the present embodiment is four in total, and has two first connecting blade surface portions 15a and two second connecting blade surface portions 15b. Further, as described above, each of the connecting blade surface portions 15 of the present embodiment is a planar blade surface portion made up of a single plane, and the two first connecting blade surface portions 15a are made up of two planar blade surface portions continuously formed. The two second connecting blade surface portions 15b are also made up of two planar blade surface portions formed continuously.

As described above, the blade surface 4 of the present embodiment includes the first blade surface portion 5, the second blade surface portion 6, the plurality of connecting blade surface portions 15, and the third blade surface portion 7. As illustrated in FIG. 2(a) and the like, the blade surface 4 has a first blade surface portion 5 and a second blade surface portion 6 on the distal end side, and has a third blade surface portion 7 on the proximal end side. Each of the first blade surface portion 5, the second blade surface portion 6, the connecting blade surface portion 15 and the third blade surface portion 7 of the present embodiment is made up of a plane. That is, the blade surface 4 of the present embodiment is provided by continuously forming the planar blade surface portions. In the hollow portion 10 of the main body portion 2, a distal end opening 11, which is one end on the distal end side of the main body portion 2, is defined by the inner edge of the blade surface 4. More specifically, the distal end opening 11 of this embodiment is defined by the inner edge of the first blade surface portion 5, the inner edge of the second blade surface portion 6, the inner edges of the plurality of connecting blade surface portions 15, and the inner edge of the third blade surface portion 7.

Here, as illustrated in FIGS. 2(a) and 2(b), the first blade surface portion 5 and the second blade surface portion 6 extend to be closer to the proximal end side of the main body portion 2 than a middle position H in the central axis direction A of the blade surface region T in which the blade surface 4 is formed. The "blade surface region T" means a region defined by the outer edge of the blade surface. In the present embodiment, the "blade surface region T" means a region defined by the outer edge of the blade surface 4, that is, a region defined by the outer edge of the first blade surface portion 5, the outer edge of the second blade surface portion 6, the outer edges of the plurality of connecting blade surface portions 15, and the outer edge of the third blade surface portion 7. Further, the "middle position H" means a position in the middle of a range in which the blade surface region T extends in the central axis direction A, and in the present embodiment, means a middle position in the central axis direction A between the needle tip 8 and the proximal end of the third blade surface portion 7.

In this way, if the first blade surface portion 5 and the second blade surface portion 6 are configured to extend to be closer to the proximal end side of the main body portion 2 than the middle position H, in the blade surface 4, it is possible to secure a relatively large length in the central axis direction A of the first blade surface portion 5 and the second blade surface portion 6 which form the blade edge 9. As long as the lengths in the central axis direction A of the first blade surface portion 5 and the second blade surface portion 6 can be increased, even if the first blade surface portion 5 and the second blade surface portion 6 are each made up of a plane, a blade tip angle α can be set to be relatively small, and it is possible to achieve the puncture needle 1 having a thin blade tip. The "blade tip angle α" used here means an angle at which the blade edge 9 intersects with the back surface of the blade edge 9 at the needle tip 8, in a side view of the main body portion 2 in which the needle tip 8 is located at one end in a direction B orthogonal to the central axis direction A (in a side view illustrated in FIGS. 1(b) and 2(b) in the puncture needle 1 of the present embodiment).

Further, in the present embodiment, both the planar first blade surface portion 5 and the planar second blade surface portion 6 extend to be closer to the proximal end side of the main body portion 2 than the middle position H, but the present invention is not limited to this configuration. The planar blade surface portion of at least one of the first blade surface portion 5 and the second blade surface portion 6 may be configured to extend to be closer to the proximal end side of the main body portion 2 than the middle position H. Therefore, only one of the first blade surface portion and the second blade surface portion is formed by a plane, and the planar blade surface portion is configured to extend to be closer to the proximal end side of the main body portion 2 than the middle position H. At the same time, the other blade surface portion may be formed by a plane or a curved surface, and the other blade surface portion may be configured not to extend to be closer to the proximal end side of the main body portion 2 than the middle position H. However, as in the present embodiment, as long as both of the planar first blade surface portion 5 and the planar second blade surface portion 6 are configured to extend to be closer to the proximal end side of the main body portion 2 than the middle position H, it is possible to more easily achieve a configuration in which the blade tip angle α is small as compared with a case where only one planar blade surface portion extends to be closer to the proximal end side of the main body portion 2 than the middle position H. Therefore, as in the present embodiment, it is preferable to provide a configuration in which both of the first blade surface portion 5 and the second blade surface portion 6 are formed by planes, and both of the first blade surface portion 5 and the second blade surface portion 6 extend to be closer to the proximal end side of the main body portion 2 than the middle position H.

The blade surface 4 may have another blade surface portion located on the proximal end side with respect to the blade surface portion of the distal end side, in addition to the blade surface portion (the first blade surface portion 5 and the second blade surface portion 6 in this embodiment) on the distal end side extending to be closer to the position of the proximal end side of the main body portion 2 from the needle tip 8 than the middle position H. The configuration of another blade surface portion is not limited to the configuration of the connecting blade surface portion 15 or the third blade surface portion 7 of the present embodiment. Therefore, for example, the third blade surface portion 7 of the present embodiment is made up of a plane, but it may be made up of a convex or concave curved surface. In the puncture needle 1 of the present embodiment, the connecting blade surface portion 15 is provided between each of the first blade surface portion 5 and the second blade surface portion 6 and the third blade surface portion 7, but the connecting blade surface portion 15 may not be included.

However, in the case of a configuration in which at least one blade surface portion of the first blade surface portion 5 and the second blade surface portion 6 extends to be closer to the proximal end side than the middle position H (see FIGS. 2(a) and 2(b)) of the blade surface region T, when the connecting blade surface portion 15 is not provided at all, there is a high possibility that a step formed by the ridge line between the one blade surface portion and the third blade surface portion increases. In such a case, there is a risk that the portion of the step becomes a large piercing resistance. Therefore, when providing the first blade surface portion 5 and the second blade surface portion 6 which extend to be closer to the proximal end side than the middle position H (see FIGS. 2(a) and 2(b)) of the blade surface region T, as in the present embodiment, it is preferable to provide the connecting blade surface portion 15 between the first blade surface portion 5 and the third blade surface portion 7 and between the second blade surface portion 6 and the third blade surface portion 7, respectively. When providing the connecting blade surface portion 15, it is possible to suppress formation of large steps between the first blade surface portion 5 and the third blade surface portion 7, and between the second blade surface portion 6 and the third blade surface portion 7.

Furthermore, as in the present embodiment, it is particularly preferable to provide a plurality of connecting blade surface portions 15 (a plurality of first connecting blade surface portions 15a and a plurality of second connecting blade surface portions 15b in the present embodiment), between the first blade surface portion 5 and the third blade surface portion 7, and between the second blade surface portion 6 and the third blade surface portion 7. In this way, it is possible to more smoothly connect between the first blade surface portion 5 and the third blade surface portion 7, and between the second blade surface portion 6 and the third blade surface portion 7, without forming a large step. Therefore, although the present embodiment is configured so that the two first connecting blade surface portions 15a and the two second connecting blade surface portions 15b are provided, a configuration in which three or more first connecting blade surface portions 15a and three or more second connecting blade surface portions 15b are included may be provided. The details of the puncture needle having three or more first connecting blade surface portions 15a and three or more second connecting blade surface portions 15b will be described later (see FIGS. 5(a) to 5(d) and the like).

Furthermore, each of the connecting blade surface portions 15 of the present embodiment is a planar blade surface portion made up of a plane, but may include a curved blade surface portion made up of a curved surface, and all the connecting blade surface portions 15 may be made up of a curved blade surface portion. Details of a configuration in which the connecting blade surface portion 15 is a curved blade surface portion will also be described later (see FIGS. 8 and 9(a) to 9(e)).

Here, the shape of the inner edge of the blade surface 4 will be described. In the side view of the puncture needle 1 illustrated in FIGS. 1(b) and 2(b), the inner edge of the blade surface 4 includes a curved portion which is curved in a concave shape and extends from one end on the needle tip 8 side of the inner edge (which is the same as the distal end side in the central axis direction A), in other words, the proximal end of the blade edge 9.

More specifically, the inner edge of the blade surface 4 has two curved portions of a first curved portion 13a made up of the inner edge of the first blade surface portion 5 and inner edges of the plurality of first connecting blade surface portions 15a, and a second curved portion 13b made up of the inner edge of the second blade surface portion 6 and the inner edges of the plurality of second connecting blade surface portions 15b. In the side views of FIGS. 1(b) and 2(b), only the second curved portion 13b is in a visible state.

As illustrated in FIG. 2(a), each of the first curved portion 13a and the second curved portion 13b extends to be closer to the proximal end side of the main body portion 2 than the middle position V of the inner edge of the blade surface 4 in the central axis direction A.

As described above, as long as the inner surface of the blade surface 4 of the puncture needle 1 is configured to have a concave curved portion in a side view (in the puncture needle 1 of the present embodiment, in aside view illustrated in FIGS. 1(b) and 2(b)) of the main body portion 2 in which the needle tip 8 is located at one end in the direction orthogonal to the central axis direction A, saprophytic bacteria or the like are hard to enter the body from the incision on the body surface as compared with the configuration with no curved portion. Specifically, when the first curved portion 13a and the second curved portion 13b pass through the incision formed on the body surface at the time of puncturing of the puncture needle 1, the edge portion of the incision is pressed in the direction of expanding the incision by the first curved portion 13a and the second curved portion 13b. In this way, when the first curved portion 13a and the second curved portion 13b pass through the body surface, it is possible to suppress the edge portion of the incision together with the blade surface 4 from being pushed into the body side by being wound in the body side, thereby reducing the risk of infection caused by saprophytic bacteria and the like.

Further, in the side views of FIG. 1(b) and FIG. 2(b), as long as a curved portion curved in a concave shape and extending from one end on the needle tip side of the inner edge of the blade surface 4 (in the present embodiment, the first curved portion 13a and the second curved portion 13b) is configured to extend to be closer to the proximal end side of the main body portion 2 than the middle position V, as compared with a configuration with no concave curved portion or a configuration in which the concave curved portion does not extend to be closer to the proximal end side than the middle position V, it is easy to achieve a configuration with a small blade tip angle α, while thinning the thickness between the blade surface 4 and the back surface of the blade surface 4, in the side view. That is, the shape of the blade surface 4 with small piercing resistance is easily achieved.

As the material of the main body portion 2, it is possible to use a metal material such as stainless steel, aluminum or aluminum alloy, titanium or a titanium alloy.

Hereinafter, the details of each configuration and characteristic part of this embodiment will be described.

[Main Body Portion 2]

The main body portion 2 of the present embodiment is a tube body in which an inner diameter of the inner circumferential surface and an outer diameter of the outer circumferential surface thereof are similar in the central axis direction A, and an end portion on the proximal end side in the central axis direction A is connected to medical instruments, such as a syringe via a needle base or the like. Therefore, the puncture needle 1 may be configured to include a needle base or the like connected to the main body portion 2.

In the main body portion 2 of the present embodiment, the inner circumferential surface defines the hollow portion 10, and the inner diameter of the inner circumferential surface and the outer diameter of the outer circumferential surface are similar in the central axis direction A, but the present invention is not limited to this configuration. For example, the inner diameter of the inner circumferential surface and the outer diameter of the outer circumferential surface of the main body portion 2 may gradually decrease toward the distal end side in the central axis direction A. Further, for example, a tapered shape in which the outer diameter of the main body portion 2 gradually decreases toward the distal end side in the central axis direction A may be provided, and the inner diameter of the main body portion 2 may be uniform in the central axis direction A. Furthermore, a part, in which the inner diameter gradually decreases or gradually increases toward the distal end side in the central axis direction A, may be provided in a partial region of the main body portion 2 in the central axis direction A. In this way, the inner diameter and the outer diameter of the main body portion 2 can adopt various configurations depending on the use of the puncture needle 1 and the like.

The puncture needle 1 of the present embodiment is a hollow needle that defines the hollow portion 10 in which the main body portion 2 communicates from the proximal end to the distal end, but may be a solid needle which does not define the hollow portion. A configuration in the case of the solid needle will be described later (see FIGS. 11(a) to 13(e)).

[First Blade Surface Portion 5 and Second Blade Surface Portion 6]

As illustrated in FIG. 2(a), each of the first blade surface portion 5 and the second blade surface portion 6 is continues with the third blade surface portion 7 via the connecting blade surface portion 15, on the proximal end side of the main body portion 2 in the central axis direction A. More specifically, the first blade surface portion 5 is continuous with the third blade surface portion 7 via the plurality of first connecting blade surface portions 15a, on the proximal end side of the main body portion 2 in the central axis direction A. The second blade surface portion 6 is continuous with the third blade surface portion 7 via the plurality of second connecting blade surface portions 15b, on the proximal end side of the main body portion 2 in the central axis direction A.

FIGS. 3(a), 3(b), 3(c), 3(d) and 3(e) are cross-sectional views taken along a line I-I, a line II-II, a line III-III, a line IV-IV and a line V-V in FIG. 2(a), respectively. The symbol "X" indicated in FIGS. 3(a) to 3(e) is a single virtual plane including the central axis O of the main body portion 2 and the needle tip 8, and is hereinafter referred to as a "central plane X". The central plane X of the present embodiment is a plane including not only the needle tip 8 but also the blade edge 9, and the main body portion 2 of the present embodiment has a symmetrical structure with the central plane X interposed therebetween. Further, in FIGS. 3(*a*) to 3(*e*), the ridge line between the blade surface portions is indicated by a solid line.

FIG. 3(*a*) is a cross-sectional view taken along the line I-I of FIG. 2(*a*), that is, a cross section orthogonal to the central axis direction A at the position where the blade edge 9 is formed in the central axis direction A. As illustrated in FIG. 3(*a*), each of the first blade surface portion 5 and the second blade surface portion 6 extends to be inclined by an angle $\theta 1$ with respect to the central plane X. The angle $\theta 1$ is preferably in the range of 45 degrees to 75 degrees, and more preferably, in the range of 50 degrees to 60 degrees. The outer edge of the first blade surface portion 5 and the outer edge of the second blade surface portion 6 are formed with cutting blades by ridge lines in which each of the first blade surface portion 5 and the second blade surface portion 6 and the outer circumferential surface of the main body portion 2 intersect with each other. However, when the angle $\theta 1$ is less than 45 degrees, a cutting blade angle $\beta$ formed by each of the first blade surface portion 5 and the second blade surface portion 6 and the outer circumferential surface of the main body portion 2 increases, and it is difficult to form a sharp cutting blade. Further, when the angle $\theta 1$ is larger than 75 degrees, in the front view of the puncture needle 1 (see FIGS. 1(*a*) and 2(*a*)), an apparent angle $\gamma 1$ (see FIG. 2(*a*)) formed between the outer edge of the first blade surface portion 5 and the needle tip 8, and an apparent angle $\gamma 2$ (see FIG. 2(*a*)) formed between the outer edge of the second blade surface portion 6 and the needle tip 8 increase, and the piercing resistance in the needle tip 8 increases.

FIG. 3(*b*) is a cross-sectional view taken along the line II-II of FIG. 2(*a*), that is, a cross-section orthogonal to the central axis direction A, which includes the first blade surface portion 5 and the second blade surface portion 6 and does not include the connecting blade surface portion 15 and the third blade surface portion 7, at a position where the distal end opening 11 exists in the central axis direction A. As illustrated in FIG. 3(*b*), an angle $\theta 2$ of each of the first blade surface portion 5 and the second blade surface portion 6 in the II-II cross-section of FIG. 2(*a*) with respect to the central plane X is equal to the angle $\theta 1$.

FIG. 3(*c*) is a cross-sectional view taken along the line III-III of FIG. 2(*a*), that is, a cross-section orthogonal to the central axis direction A, which includes the first blade surface portion 5, the second blade surface portion 6 and the connecting blade surface portion 15, and does not include the third blade surface portion 7, at a position where the distal end opening 11 exists in the central axis direction A. As illustrated in FIG. 3(*c*), an angle $\theta 3$ of each of the first blade surface portion 5 and the second blade surface portion 6 in the III-III cross-section of FIG. 2(*a*) with respect to the central plane X is equal to the angle $\theta 1$ and the angle $\theta 2$.

As described above, the angle $\theta$ of each of the first blade surface portion 5 and the second blade surface portion 6 with respect to the central plane X in the cross-section orthogonal to the central axis direction A is constant regardless of the position in the central axis direction A.

[Connecting Blade Surface Portion 15]

As described above, the plurality of connecting blade surface portions 15 of the present embodiment includes a plurality of first connecting blade surface portions 15*a* which connects the first blade surface portion 5 and the third blade surface portion 7, and a plurality of second connecting blade surface portions 15*b* which connects the second blade surface portion 6 and the third blade surface portion 7. Further, each of the connecting blade surface portions 15 in the present embodiment is a planar blade surface portion made up of a plane. As illustrated in FIGS. 1(*a*), 2(*a*), and the like, the outline of each connecting blade surface portion 15 in the circumferential direction of the distal end opening 11 is a ridge line formed between adjacent blade surface portions, and the ridge lines located on both circumferential sides of the distal end opening 11 of each connecting blade surface portion 15 extend along the central axis O. In other words, each connecting blade surface portion 15 defined by the ridge lines located on both circumferential sides of the distal end opening 11 also extends along the central axis O. The length of each connecting blade surface portion 15 in the extending direction along the central axis O is longer than the length (hereinafter referred to as "width") in the direction orthogonal to the extending direction. That is, each connecting blade surface portion 15 has an elongated shape which is elongated in the extending direction along the central axis O. Furthermore, in the front view illustrated in FIGS. 1(*a*) and 2(*a*), each of the connecting blade surface portions 15 has a shape in which the width gradually increases toward the proximal end side in the extending direction along the central axis O.

In the present application, the meaning of the expression "along the central axis O" includes not only a state of being substantially parallel to the central axis O but also a state (30 degrees or less) in which the angle formed to the central axis O is relatively small.

In this way, as long as the ridge line formed between each connecting blade surface portion 15 and the blade surface portion adjacent to the connecting blade surface portion 15 is configured to extend along the central axis O, it is possible to suppress an increase in piercing resistance caused by the ridge line portion, as compared with a configuration in which the ridge line extends without following the central axis O.

Next, in the present embodiment, a specific example of the ridge line formed between each connecting blade surface portion 15 and the blade surface portion adjacent to the connecting blade surface portion 15, and the extending direction thereof will be described.

First, there are two first connecting blade surface portions 15*a* in the present embodiment, and as illustrated in FIG. 2(*a*), the two first connecting blade surface portions 15*a* include a first connecting blade surface portion 15*a*1 on the distal end side which is continuous with the first blade surface portion 5 with the ridge lines intersecting with each other as a boundary, and a first connecting blade surface portion 15*a*2 on the proximal end side which is continuous with the third blade surface portion 7 with the ridge lines intersecting with each other as a boundary. The first connecting blade surface portion 15*a*1 on the distal end side and the first connecting blade surface portion 15*a*2 on the proximal end side are continuous with each other with the ridge lines intersecting with each other as a boundary.

Further, there are also two second connecting blade surface portions 15*b* in this embodiment, and as illustrated in FIG. 2(*a*), the two second connecting blade surface portions 15*b* include a second connecting blade surface portion 15*b*1 on the distal end side which is continuous with the second blade surface portion 6 with the ridge lines intersecting with each other as a boundary, and a second connecting blade surface portion 15*b*2 on the proximal end side which is continuous with the third blade surface portion 7 with the ridge lines intersecting with each other as a boundary. The second connecting blade surface portion 15*b*1 on the distal end side and the second connecting blade surface portion 15*b*2 on the proximal end side are continuous with each other with the ridge lines intersecting with each other as a boundary.

When the ridge line between each connecting blade surface portion 15 and another blade surface portion (the first blade surface portion 5, the second blade surface portion 6, the connecting blade surface portion 15 or the third blade surface portion 7 in this embodiment) adjacent to the connecting blade surface portion 15 is provided as a "ridge portion", details of the extending direction of each ridge portion in the present embodiment will be described.

In the present embodiment, a first ridge portion 16 between the first blade surface portion 5 and the first connecting blade surface portion 15*a*1 on the distal end side extends along the central axis O. A second ridge portion 17 between the first connecting blade surface portion 15*a*1 on the distal end side and the first connecting blade surface portion 15*a*2 on the proximal end side also extends along the central axis O. Furthermore, a third ridge portion 18 between the third blade surface portion 7 and the first connecting blade surface portion 15*a*2 on the proximal end side also extends along the central axis O.

Furthermore, a fourth ridge portion 19 between the second blade surface portion 6 and the second connecting blade surface portion 15*b*1 on the distal end side, a fifth ridge portion 20 between the second connecting edge portion 15*b*1 on the distal end side and the second connecting edge portion 15*b*2 on the proximal end side, and a sixth ridge portion 21 between the third blade surface portion 7 and the second connecting blade surface portion 15*b*2 on the proximal end side also extend along the central axis O.

In this way, in the present embodiment, all the ridge portions (the first ridge portion 16, the second ridge portion 17, the third ridge portion 18, the fourth ridge portion 19, the fifth ridge portion 20, and the sixth ridge portion 21 in the present embodiment) extend along the central axis O.

In the present embodiment, all of the first ridge portion 16, the second ridge portion 17, the third ridge portion 18, the fourth ridge portion 19, the fifth ridge portion 20, and the sixth ridge portion 21 extend along the central axis O. However, the present invention is not limited to this configuration, and only a part of the ridge portion may extend along the central axis O. In such a case, for the purpose of suppressing an increase in piercing resistance at the inner edge (sometimes referred to as a heel portion of the blade surface 4) of the blade surface 4 on the proximal end side of the distal end opening 11, it is preferable to provide a configuration in which the ridge portions close to the proximal end of the inner edge of the blade surface 4, that is, the third ridge portion 18 and the sixth ridge portion 21 formed by the ridge lines in which the third blade surface portion 7 and the connecting blade surface portion 15 intersect with each other in this embodiment at least extend along the central axis O. However, considering all piercing resistance occurring at the time of puncturing, it is particularly preferable to provide a configuration in which all the ridge portions formed by providing the connecting blade surface portion 15 are arranged along the central axis O as in this embodiment.

Further, one end on the proximal end side of the main body portion 2 among the ridge portions formed between the third blade surface portion 7 and the connecting blade surface portion 15 is located between one end (see a point "R1" in FIG. 2(*a*)) on the proximal end side of the main body portion 2 at the inner edge of the blade surface 4, and the proximal end of the blade surface 4 (see a point "R2" in FIG. 2(*a*)) in the central axis direction A. Further, the proximal end of the blade surface 4 refers to one end on the proximal end side of the main body portion 2 at the outer edge of the blade surface 4.

More specifically, one ends on the proximal end side of the third ridge portion 18 and the sixth ridge portion 21 of the present embodiment are located between the point R1 and the point R2 illustrated in FIG. 2(*a*) in the central axis direction A. However, one end on the proximal end side of the main body portion 2 of all the ridge portions is more preferably located between the point R1 as one end on the proximal end side of the main body portion 2 at the inner edge of the blade surface 4 and the point R2 as the proximal end of the blade surface 4, in the central axis direction A. As long as the connecting blade surface portion 15 for smoothly connecting the first blade surface portion 5, the second blade surface portion 6 and the third blade surface portion 7 is formed so that the ridge portions have such a configuration, it is possible to secure a larger ratio of the first blade surface portion 5 and the second blade surface portion 6 in the central axis direction A in the blade surface region T. This makes it easier to achieve a blade surface shape with a smaller blade tip angle $\alpha$. The puncture needle having a configuration in which one ends on the proximal end side of all the ridge portions are located between the one end on the proximal end side of the inner edge of the blade surface and the proximal end of the blade surface in the central axis direction A will be described below in detail (see FIGS. 10(*a*) and 10(*b*) and the like).

Further, as illustrated in FIG. 2(*a*), in a front view, an angle $\rho 1$ (for example, an angle formed between an extension line U and the central axis O indicated by a two-dot chain line in FIG. 2(*a*)) of the ridge portion extending along the central axis O with respect to the central axis O is preferably smaller than an angle $\rho 2$ of an imaginary straight line D1 passing through the point N on the outer edge of the first blade surface portion 5 or the second blade surface portion 6 and the needle tip 8 with respect to the central axis O in the same front view. Here, the point N on the outer edge of the first blade surface portion 5 or the second blade surface portion 6 is a point in which an imaginary straight line D2 passing through the proximal end of the blade edge 9 and orthogonal to the central axis direction A intersects with the outer edge of the first blade surface portion 5 or the second blade surface portion 6. In FIG. 2(*a*), the imaginary straight line D2 is indicated by a two-dot chain line. In FIG. 2(*a*), the point N is a point on the outer edge of the second blade surface portion 6, but it may be a point on the outer edge of the first blade surface portion 5.

Furthermore, the plurality of first connecting blade surface portions 15*a* in the present embodiment is continuous along the circumferential direction of the distal end opening 11 in the front view illustrated in FIGS. 1(*a*) and 2(*a*). In other words, the plurality of first connecting blade surface portions 15*a* is continuous in a width direction orthogonal to the extending direction which extends along the central axis O. Further, the plurality of second connecting blade surface portions 15*b* in the present embodiment is also continuous along the circumferential direction of the distal end opening 11 in the same front view. In other words, the plurality of second connecting blade surface portions 15*b* is also continuous in the width direction.

In the central axis direction A, the ratio of the lengths of the first blade surface portion 5 and the second blade surface portion 6 with respect to the length of the blade surface region T is preferably greater than 50% and is equal to or less than 95%, and more preferably, is greater than 50% and equal to or less than 60%. When the ratio of the first blade surface portion 5 and the second blade surface portion 6 is greater than 95%, even if the connecting blade surface portion 15 is formed, a large step is formed between the third blade surface portion 7 and the connecting blade surface portion 15, and it is difficult to reduce the piercing resistance.

Hereinafter, the configuration of the connecting blade surface portion 15 in the cross section orthogonal to the central axis direction A will be described.

Figure 3A:
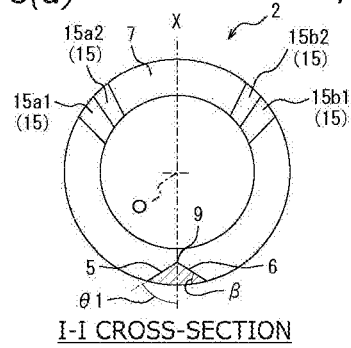
FIGS. 3(a), 3(b), 3(c), 3(d) and 3(e) are cross-sectional views taken along a line I-I, a line II-II, a line III-III, a line IV-IV and a line V-V in FIG. 2(a), respectively.
Figure 3B:
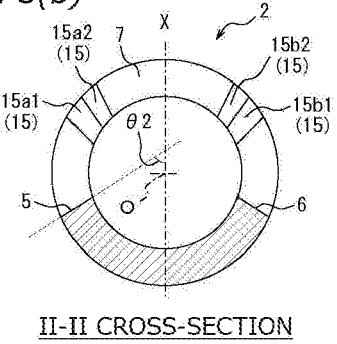
Figure 3C:
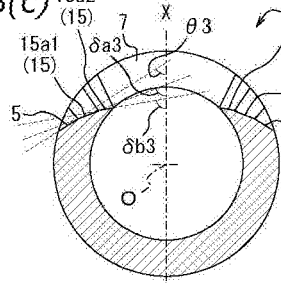

As illustrated in FIG. 3(c), each of the first connecting blade surface portion 15a1 on the distal end side and the second connecting blade surface portion 15b1 on the distal end side in the III-III cross section of FIG. 2(a) extends to be inclined with respect to the central plane X at an angle δa3. Further, each of the first connecting blade surface portion 15a2 on the proximal end side and the second connecting blade surface portion 15b2 on the proximal end side in the same cross section extends to be inclined at an angle δb3 with respect to the central plane X. Here, the angle δb3 is larger than the angle δa3 and larger than the aforementioned angles θ1 to θ3. The angle δa3 is also larger than the aforementioned angles θ1 to θ3.

Figure 3D:
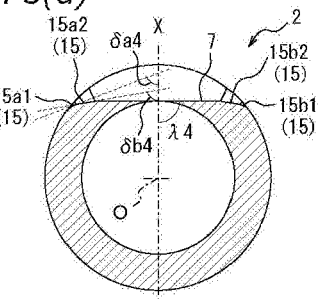

FIG. 3(d) is a cross-sectional view taken along the line IV-IV of FIG. 2(a), that is, a cross section orthogonal to the central axis direction A which includes the connecting blade surface portion 15 and the third blade surface portion 7, and does not include the first blade surface portion 5 and the second blade surface portion 6, at the position of the proximal end of the distal end opening 11 in the central axis direction A. As illustrated in FIG. 3(d), each of the first connecting blade surface portion 15a1 on the distal end side and the second connecting blade surface portion 15b1 on the distal end side in the IV-IV cross section of FIG. 2(a) extends to be inclined with respect to the central plane X at an angle δa4. Further, each of the first connecting blade surface portion 15a2 on the proximal end side and the second connecting blade surface portion 15b2 on the proximal end side in the same cross section extends to be inclined with respect to the central plane X at an angle δb4.

Here, the angle δa3 in FIG. 3(c) is equal to the angle δa4 in FIG. 3(d). The angle δb3 in FIG. 3(c) is equal to the angle δb4 in FIG. 3(d). In this way, the angle δa of each of the first connecting blade surface portion 15a1 on the distal end side and the second connecting blade surface portion 15b1 on the distal end side in the cross section orthogonal to the central axis direction A with respect to the central plane X is constant irrespective of the position in the central axis direction A. Further, the angle δb of each of the first connecting blade surface portion 15a2 on the proximal end side and the second connecting blade surface portion 15b2 on the proximal end side in the cross section orthogonal to the central axis direction A with respect to the central plane X is constant, irrespective of the position in the central axis direction A.

In this way, the first blade surface portion 5 and the third blade surface portion 7 are smoothly connected by the first connecting blade surface portion 15a1 on the distal end side and the first connecting blade surface portion 15a2 on the proximal end side. Further, the second blade surface portion 6 and the third blade surface portion 7 are smoothly connected by the second connecting blade surface portion 15b1 on the distal end side and the second connecting blade surface portion 15b2 on the proximal end side.

[Blade Edge 9]

As described above, the blade edge 9 is formed by a ridge line in which the first blade surface portion 5 and the second blade surface portion 6 intersect with each other. Further, as described above, the blade edge 9 of the present embodiment extends on the central plane X, and the needle tip 8 which is one end of the blade edge 9 is also located on the central plane X.

If the distal end of the puncture needle 1 is configured to be sharpened to provide the blade edge 9 as in the present embodiment, when the puncture needle 1 is punctured into the human body, the blade edge 9, or the outer edge of the first blade surface portion 5 near the blade edge 9 and the outer edge of the second blade surface portion 6, act as a cutting blade for cutting the skin, and it is possible to reduce the resistance applied to the skin during puncture. Therefore, it is possible to reduce the pain sensed by a patient or the like into which the puncture needle 1 is punctured.

[Third Blade Surface Portion 7]

The third blade surface portion 7 of the present embodiment is made up of a plane. Specifically, the third blade surface portion 7 is a linear plane which is inclined to approach the central axis O toward the needle tip 8 in the central axis direction A as viewed from the side of FIG. 2(b). The inclination angle of the third blade surface portion 7 to the central axis direction A is larger than the inclination angle of the outer circumferential surface of the main body portion 2 to the central axis direction A in the cross section including the entire central axis O.

In the present embodiment, the outer diameter of the main body portion 2 of the puncture needle 1 is uniform in the central axis direction A, and when viewed in a cross section including the entire central axis O, the outer circumferential surface of the main body portion 2 extends in the central axis direction A. Therefore, if the third blade surface portion 7 is inclined with respect to the central axis direction A, the inclination angle of the third blade surface portion 7 becomes larger than the inclination angle of the outer wall of the main body portion 2. However, when the main body portion of the puncture needle is configured to gradually decrease or gradually increase toward the distal end side in the central axis direction A, the third blade surface portion is configured not only to be inclined with respect to the central axis direction A, but also to be inclined with respect to the outer circumferential surface of the main body portion 2 in the cross section including the entire central axis O.

Although the third blade surface portion 7 of this embodiment is a plane, the third blade surface portion may be made up of a curved surface as described above. In such a case, the above-mentioned "inclination angle of the third blade surface portion to the central axis direction" refers to an angle formed between a tangential line at an arbitrary point on the third blade surface portion and the central axis, in the cross section passing through the third blade surface portion including the entire central axis line.

Next, a configuration of the third blade surface portion 7 in the cross section orthogonal to the central axis direction A will be described.

As illustrated in FIG. 3(d), an angle λ4 of the third blade surface portion 7 with respect to the central plane X in the IV-IV cross section of FIG. 2(a) is about 90 degrees. In other words, in the IV-IV cross-section of FIG. 2(a), the third blade surface portion 7 extends linearly in a direction orthogonal to the central plane X.

Figure 3E:
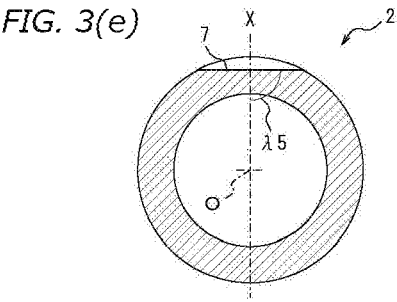

FIG. 3(e) is a cross-sectional view taken along the line V-V of FIG. 2(a), that is, a cross section orthogonal to the central axis direction A, including only the third blade surface portion 7, at a position that is closer to the proximal end side than the distal end opening 11 in the central axis direction A. As illustrated in FIG. 3(*e*), an angle λ5 of the third blade surface portion 7 in the V-V cross-section of FIG. 2(*a*) with respect to the central plane X is about 90 degrees. In other words, in the V-V cross-section of FIG. 2(*a*), the third blade surface portion 7 extends linearly in a direction orthogonal to the central plane X.

As described above, the angle λ of the third blade surface portion 7 in the cross-section orthogonal to the central axis direction A with respect to the central plane X is constant at about 90 degrees, irrespective of the position in the central axis direction A (see FIGS. 3(*d*) and 3(*e*)).

Further, an angle variation between the angle θ of the first blade surface portion 5 and the angle δa of the first connecting blade surface portion 15*a* on the distal end side, an angle variation between the angle δa of the first connecting blade surface portion 15*a*1 on the distal end side and the angle δb of the first connecting blade surface portion 15*a*2 on the proximal end side, and an angle variation between the angle δb between the first connecting blade surface portion 15*a*2 on the proximal end side and the angle λ of the third blade surface portion 7 can be set to an approximately equal level. Further, the three angle variations may gradually decrease or gradually increase from the first blade surface portion 5 toward the third blade surface portion 7. The same also applies to the angular relationship among the second blade surface portion 6, the second connecting blade surface portion 15*b*1 on the distal end side, the second connecting blade surface portion 15*b*2 on the proximal end side, and the third blade surface portion 7.

[Shape of Blade Surface 4 in Side View]

As described above, the puncture needle 1 of the present embodiment is provided with the main body portion 2 having the blade surface 4 formed at the distal end portion 3, and the blade surface 4 has the first blade surface portion 5, the second blade surface portion 6, the plurality of connecting blade surface portions 15 and the third blade surface portion 7. Further, the inner edge of the blade surface 4 has a first curved portion 13*a* and a second curved portion 13*b* that have a concave shape in the side views of FIGS. 1(*b*) and 2(*b*). The blade surface 4 and other features thereof in the side view will be described below.

Figure 4:
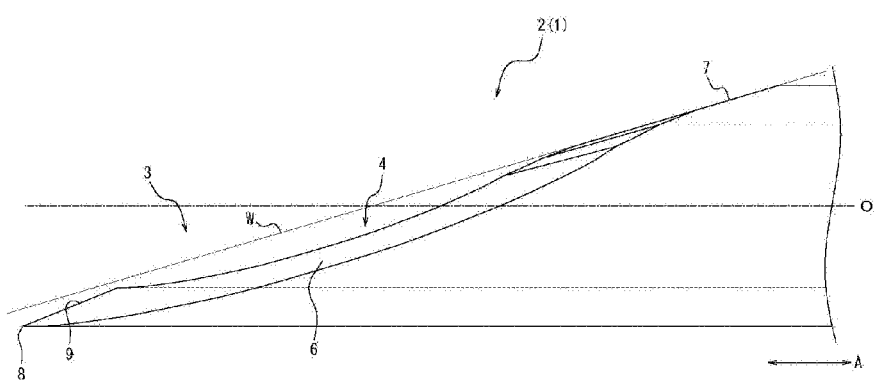
FIG. 4 is an enlarged side view illustrating the vicinity of the distal end portion in FIG. 2(b) in a further enlarged manner.

FIG. 4 is an enlarged side view illustrating the vicinity of the distal end portion 3 in FIG. 2(*b*) in a further enlarged manner. The distal end of the inner edge of the blade surface 4 of the present embodiment is not located on the extension line W of the third blade surface portion 7 in the side view of FIG. 4. More specifically, in the side view of FIG. 4, the proximal end of the blade edge 9, which is the distal end of the inner edge of the blade surface 4 of the present embodiment, is located to be closer to the needle tip 8 side than the extension line W of the third blade surface portion 7, and there is a gap between the proximal end of the blade edge 9 and the extension line W.

Further, in the puncture needle 1 of the present embodiment, in a side view (see FIG. 2(*b*) and the like) in which the needle tip 8 is located at one end in a direction orthogonal to the central axis direction A, a straight line L (see a two-dot chain line in FIG. 2(*b*)) passing through the needle tip 8 and the point K as the proximal end of the blade surface 4 is inclined at an angle (see the blade surface angle "Z" in FIG. 2(*b*)) of 13 degrees or more and 20 degrees or less with respect to the central axis O. Further, the point K, which is the proximal end of the blade surface 4 through which the straight line L passes, is a point R2 (see FIG. 2(*a*)) representing the proximal end on the third blade surface portion 7 in the present embodiment. With such a configuration, the blade surface length of the blade surface 4 in the central axis direction A (which is equal to the length of the blade surface region T in the central axis direction A) is set to be shorter than the blade surface length of a so called a "regular bevel" (a puncture needle formed with a blade surface in which an inclination angle measured by the same method as described above is 12 degrees) which is mainly used for intramuscular injection or the like, while setting the blade surface length to be approximately the same as the blade surface length of a so-called "short bevel" (a puncture needle formed with a blade surface in which an inclination angle measured by the same method as described above is approximately 18 degrees) which is mainly used for intravenous injection or the like, the blade tip angle α can be set to an angle which is equal to or less than the "regular bevel".

That is, it is possible to achieve the puncture needle 1 in which the piercing resistance at the blade surface 4 can be reduced and the vessel can be easily secured, while having a short blade surface length in which penetration of a vessel such as a vein is hard to occur. Since the piercing resistance in the vicinity of the needle tip 8 can be reduced, the amount of variation in the piercing resistance can be reduced, and it is also possible to reduce the amount of variance in the force applied by a medical staff in the puncture direction at the time of puncturing. Therefore, it is possible to achieve the puncture needle 1 which can be easily operated by the medical staff at the time of puncturing.

Further, it is preferable to set the angle of the straight line L with respect to the central axis O illustrated in FIG. 2(*b*) to the blade tip angle α of 15 degrees to 27 degrees, while setting the angle to 13 degrees or more and 20 degrees or less. When the blade tip angle α is less than 15 degrees, since the blade tip becomes too thin, there is a risk that a predetermined performance cannot be satisfied due to a damage or the like in the manufacturing process, which makes manufacturing difficult. Further, when the angle exceeds 27 degrees, since it is equivalent to the blade tip angle α of a so-called short bevel, the piercing resistance at the time of puncturing increases.

Further, in the present embodiment, the proximal end (see the point "R1" in FIG. 2(*a*)) of the inner edge of the blade surface 4 is provided on the inner edge of the third blade surface portion 7. Further, the inner edge of the blade surface 4 extends from the distal end side of the main body portion 2 toward the proximal end side, in the range from the distal end to the proximal end thereof. More specifically, in this embodiment, among the two points in which the inner edge of the blade surface 4 intersects with the central plane X, the point on the distal end side of the main body portion 2 is the distal end of the inner edge of the blade surface 4, and the point on the proximal end side of the main body portion 2 is the proximal end of the inner edge of the blade surface 4. The inner edge of the blade surface 4 always extends from the distal end side to the proximal end side of the main body portion 2, in the range from the distal end to the proximal end of the inner edge of the blade surface 4. The distal end opening 11 is in the form of a teardrop when viewed from the front.

Second Embodiment

Next, a puncture needle 101 as another embodiment different from the puncture needle 1 of the aforementioned first embodiment will be described. The puncture needle 101 of the present embodiment differs from the aforementioned puncture needle 1 in a configuration of a connecting blade surface portion 115, but other configurations are similar.

Figure 5A:
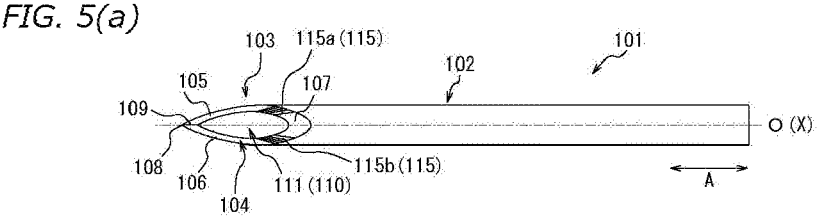
FIGS. 5(a), 5(b), 5(c) and 5(d) are a plan view and a side view of a front side of a puncture needle, and a plan view and a perspective view of a back side thereof, as an embodiment of the present invention, respectively.
Figure 5B:
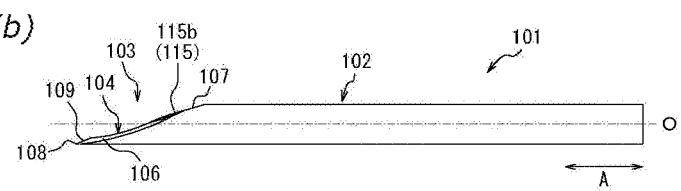
Figure 5C:
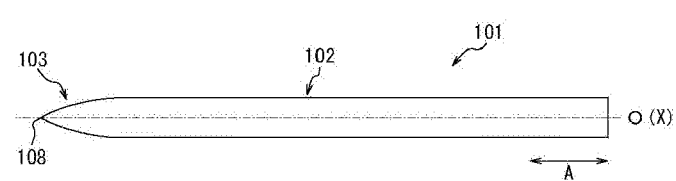
Figure 5D:
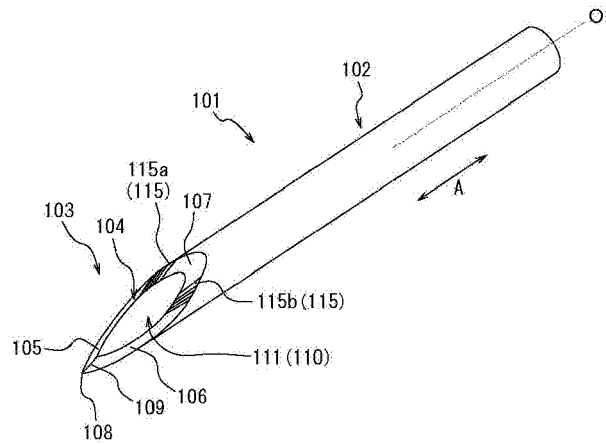

FIGS. 5(a) to 5(d) are views illustrating the puncture needle 101. Specifically, FIG. 5(a) is a plan view of the front side of the puncture needle 101, FIG. 5(b) is a side view of the puncture needle 101, and FIG. 5(c) is a plan view of the back side of the puncture needle 101. FIG. 5(d) is a perspective view of the puncture needle 101. FIGS. 6(a) and 6(b) are enlarged views of the vicinity of a distal end portion 103 of a main body portion 102 illustrated in FIGS. 5(a) and 5(b), respectively.

As illustrated in FIGS. 5(a) to 5(d) and FIGS. 6(a) and (b), a blade surface 104 is formed at the distal end portion 103 of the main body portion 102 of the puncture needle 101, and the blade surface 104 includes a first blade surface portion 105, a second blade surface portion 106, a plurality of connecting blade surface portions 115, and a third blade surface portion 107. The first blade surface portion 105 and the second blade surface portion 106 form a blade edge 109 with a needle tip 108 as one end, by ridge lines which intersect with each other. The main body portion 102 defines a hollow portion 110 with a distal end opening 111 as one end. The configurations of the first blade surface portion 105, the second blade surface portion 106 and the third blade surface portion 107 of the puncture needle 101 are the same as those of the first blade surface portion 5, the second blade surface portion 6 and the third blade surface portion 7 of the aforementioned puncture needle 1. Thus, the description thereof will not be provided here. The puncture needle 101 is different from the aforementioned puncture needle 1 in the number of connecting blade surface portions.

Specifically, the aforementioned puncture needle 1 has the two first connecting blade surface portions 15a and the two second connecting blade surface portions 15b, whereas the puncture needle 101 has four first connecting blade surface portions 115a and four second connecting blade surface portions 115b. By increasing the number of the first connecting blade surface portions and the second connecting blade surface portions in this way, it is possible to more smoothly connect a part between the first blade surface portion 105 and the third blade surface portion 107, and a part between the second blade surface portion 106 and the third blade surface portion 107.

FIGS. 7(a), 7(b), 7(c), 7(d) and 7(e) are cross-sectional views taken along a line VI-VI, a line VII-VII, a line VIII-VIII, a line IX-IX and a line X-X in FIG. 6(a), respectively. In the cross-sectional views illustrated in FIGS. 7(a) to 7(e), angles θ6 to θ8 of the first blade surface portion 105 and the second blade surface portion 106 with respect to the central plane X are equal angles, and angles λ9 and λ10 of the third blade surface portion 107 with respect to the central plane X are both equal angles at about 90 degrees. As illustrated in FIGS. 7(c) and 7(d), the first blade surface portion 105 and the third blade surface portion 107 are smoothly connected to each other by the four first connecting blade surface portions 115a so as not to form a ridge line which serves as a large step. Similarly, the second blade surface portion 106 and the third blade surface portion 107 are smoothly connected to each other by the four second connecting blade surface portions 115b so as not to form a ridge line which serves as a large step. In FIGS. 7(a) to 7(e), the ridge lines between the blade surface portions are indicated by a solid line.

In this way, the number of the connecting blade surface portions 115 which connect the first blade surface portion 105, the second blade surface portion 106 and the third blade surface portion 107 can be three or more as in the present embodiment, and by increasing the number of the connecting blade surface portions 115, it is possible to more smoothly connect the first blade surface portion 105, the second blade surface portion 106 and the third blade surface portion 107, and it is possible to further reduce the piercing resistance in a portion of the ridge line between the blade surface portions, that is, the ridge portion.

Figure 8:
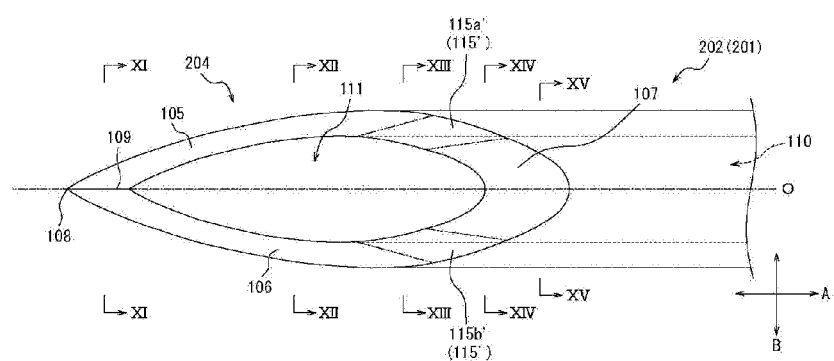
FIG. 8 is a view illustrating a modified example of the puncture needle illustrated in FIGS. 6(a) and 6(b).
Figure 9A:
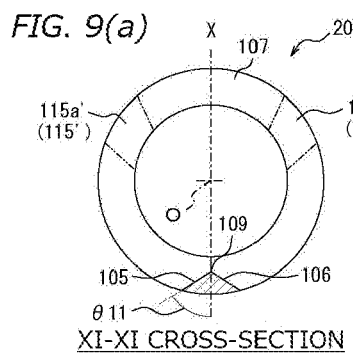
FIGS. 9(a), 9(b), 9(c), 9(d) and 9(e) are cross-sectional views taken along a line XI-XI, a line XII-XII, a line XIII-XIII, a line XIV-XIV and a line XV-XV in FIG. 8, respectively.
Figure 9B:
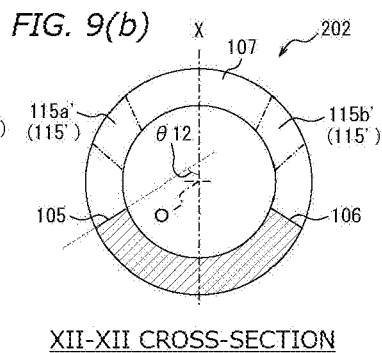
Figure 9C:
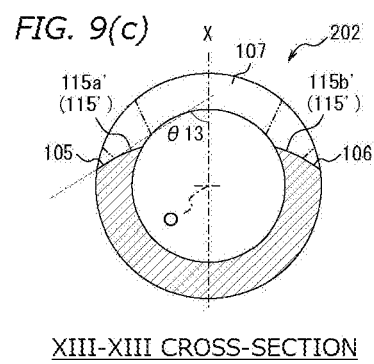
Figure 9D:
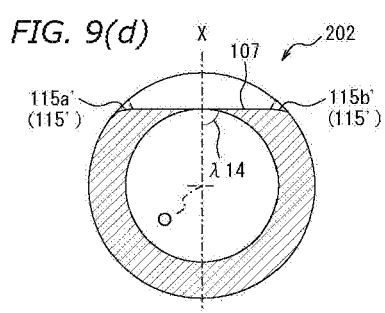
Figure 9E:
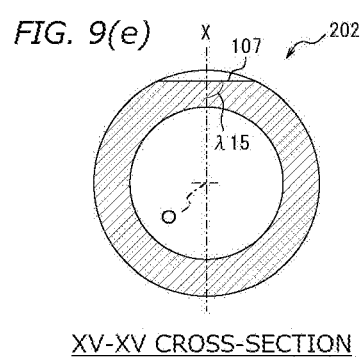

In the puncture needle 1 of the aforementioned first embodiment and the puncture needle 101 of the present embodiment, each connecting blade surface portion is a planar blade surface portion made up of a plane, but the connecting blade surface portion may also be a curved blade surface portion made up of a curved surface. FIG. 8 is an enlarged plan view on the front side illustrating a puncture needle 201 having a blade surface 204 in which all the four planar first connecting blade surface portions 115a illustrated in FIGS. 5(a) to 7(e) are changed into a single curved first connecting blade surface portion 115a', and all the four planar second connecting blade surface portions 115b illustrated in FIGS. 5(a) to 7(e) are changed into a single curved second connecting blade surface portion 115b'. Other configurations of the main body portion 202 of the puncture needle 201 illustrated in FIG. 8 are the same as those of the main body portion 102 of the puncture needle 101 illustrated in FIGS. 5(a) to 7(e).

FIGS. 9(a), 9(b), 9(c), 9(d) and 9(e) are cross-sectional views taken along a line XI-XI, a line XII-XII, a line XIII-XIII, a line XIV-XIV and a line XV-XV in FIG. 8, respectively. The first blade surface portion 105 and the second blade surface portion 106 (see FIGS. 9(a) to 9(c)) inclined at angles θ11 to θ13 (θ11 to θ13 are equal to one another) with respect to the central plane X are smoothly connected by the third blade surface portion 107 (see FIGS. 9(d) and 9(e)) extending at angles λ14 and λ15 (λ14 and λ15 are equal to each other at about 90 degrees) with respect to the central plane X, and a single first connecting blade surface portion 115a' and a single second connecting blade surface portion 115b' made up of a curved surface (see FIGS. 9(c) and 9(d)).

Further, the examples illustrated in FIG. 8 and FIGS. 9(a) to 9(e) are configured so that each of the part between the first blade surface portion 105 and the third blade surface portion 107 and the part between the second blade surface portion 106 and the third blade surface portion 107 is connected only by the connecting blade surface portion 115' made up of a curved surface, but the present invention is not limited to this configuration. For example, each of the part between the first blade surface portion 105 and the third blade surface portion 107, and the part between the second blade surface portion 106 and the third blade surface portion 107 may be provided as a plurality of connecting blade surface portions which is formed by connecting both of a planar blade surface portion made up of a plane and a curved blade surface portion made up of a curved surface. However, as illustrated in FIG. 8 and FIGS. 9(a) to 9(e), if each of the part between the first blade surface portion 105 and the third blade surface portion 107 and the part between the second blade surface portion 106 and the third blade surface portion 107 is configured to be connected by a single curved connecting blade surface portion 115' (in the example of FIG. 8 and FIGS. 9(a) to 9(e), the first connecting blade surface portion 115a' and the second connecting blade surface portion 115b'), it is possible to more smoothly connect between the first blade surface portion 105, the second blade surface portion 106 and the third blade surface portion 107 so as to form a ridge line having an extremely small step which does not become a piercing resistance or so as not to form the ridge line. In FIG. 8 and FIGS. 9(*a*) to 9(*e*), for convenience of description, a boundary between the first blade surface portion 105 and the first connecting blade surface portion 115*a*', a boundary between the second blade surface portion 106 and the second connecting blade surface portion 115*b*', and a boundary between the first connecting blade surface portion 115*a*', the second connecting blade surface portion 115*b*' and the third blade surface portion 107 are indicated by a two-dot chain line, but these boundaries do not represent a ridge line between the blade surface portions.

Further, the puncture needle according to the present invention can be achieved by various specific configurations, and is not limited to the configurations illustrated in the description of the first and second embodiments.

For example, the plurality of first connecting blade surface portions 115*a* and the plurality of second connecting blade surface portions 115*b* of the puncture needle 101 illustrated in the second embodiment are disposed such that the connecting blade surface portions having the substantially equal widths in the circumferential direction of the distal end opening 111 are continuously disposed. However, it is also possible to adopt a configuration in which the connecting blade surface portions having different widths in the circumferential direction of the distal end opening 111 are continuously disposed. FIGS. 10(*a*) and 10(*b*) illustrate a puncture needle 301 in which the first connecting blade surface portion 315*a*, which is closest to the proximal end side and continuous with the third blade surface portion 307, among the plurality of first connecting blade surface portions 315*a* is made wider than the other first connecting blade surface portion 315*a*, and the second connecting blade surface portion 315*b*, which is closest to the proximal end side and continuous with the third blade surface portion 307, among the plurality of second connecting blade surface portions 315*b* is made wider than the other second connecting blade surface portion 315*b*. Specifically, FIG. 10(*a*) is a plan view of the front side in the vicinity of the distal end portion 303 of the main body portion 302 of the puncture needle 301, and FIG. 10(*b*) is a perspective view of the vicinity of the distal end portion 303 in the main body portion 302 of the puncture needle 301.

As illustrated in FIGS. 10(*a*) and 10(*b*), the blade surface 304 in the distal end portion 303 of the main body portion 302 of the puncture needle 301 includes a first blade surface portion 305, a second blade surface portion 306, a plurality of connecting blade surface portions 315, and a third blade surface portion 307. The first blade surface portion 305 and the second blade surface portion 306 form a blade edge 309 with a needle tip 308 as one end by ridge lines that intersect with each other. Further, the main body portion 302 defines a hollow portion 310 with the distal end opening 311 as one end. The first blade surface portion 305 and the second blade surface portion 306 of the puncture needle 301 have the same configurations as those of the first blade surface portion 5 and the second blade surface portion 6 described in the first embodiment, and the first blade surface portion 105 and the second blade surface portion 106 described in the second embodiment. Thus, the description thereof will not be provided here.

As illustrated in FIGS. 10(*a*) and 10(*b*), the third blade surface portion 307 is connected to the first blade surface portion 305 via a plurality of first connecting blade surface portions 315*a*. Further, the third blade surface portion 307 is connected to the second blade surface portion 306 via a plurality of second connecting blade surface portions 315*b*. Further, the ridge portion 318 formed by the ridge line between the first connecting blade surface portion 315*a* located to be closest to the proximal end side among the plurality of first connecting blade surface portions 315*a* and the third blade surface portion 307 extends toward the proximal end side of the main body portion 302 along the central axis O from the position which is the proximal end of the distal end opening 311 among the inner edges of the blade surface 304 such that an angle with the central axis O in a plan view of FIG. 10(*a*) is 30 degrees or less. Further, a ridge portion 321 formed by a ridge line between the second connecting blade surface portion 315*b* located to be closest to the proximal end side among the plurality of second connecting blade surface portions 315*b* and the third blade surface portion 307 extends toward the proximal end side of the main body portion 302 along the central axis O from the position which is the proximal end of the distal end opening 311 among the inner edges of the blade surface 304, on the opposite side to the ridge portion 318 across the central axis O such that an angle with the central axis O in a plan view of FIG. 10(*a*) is 30 degrees or less.

In other words, in the plan view of FIG. 10(*a*), the third blade surface portion 307 has a substantially fan shape defined by a boundary between the ridge portion 318, the ridge portion 321, and the outer circumferential surface of the main body portion 302.

In the plurality of first connecting blade surface portions 315*a* illustrated in FIGS. 10(*a*) and 10(*b*), the width in the circumferential direction of the distal end opening 311 of the first connecting blade surface portion 315*a* continuous with the third blade surface portion 307 and closest to the proximal end side is larger than the width in the circumferential direction of the distal end opening 311 of other first connecting blade surface portion 315*a* (the three first connecting blade surface portions 315*a* in FIGS. 10(*a*) and 10(*b*)). Further, in the plurality of second connecting blade surface portions 315*b* illustrated in FIGS. 10(*a*) and 10(*b*), the width in the circumferential direction of the distal end opening 311 of the second connecting blade surface portion 315*b* which is continuous with the third blade surface portion 307 and closest to the proximal end side is larger than the width in the circumferential direction of the distal end opening 311 of other second connecting blade surface portions 315*b* (the three second connecting blade surface portions 315*b* in FIGS. 10(*a*) and 10(*b*)). In this way, in order to more smoothly connect the first blade surface portion 305 and the second blade surface portion 306 to the third blade surface portion 307, a configuration may be provided by continuing the plurality of first connecting blade surface portions 315*a* having different widths, and by continuing the plurality of second connecting blade surface portions 315*b* having different widths.

In the example illustrated in FIGS. 10(*a*) and 10(*b*), the first blade surface portion 305 and the second blade surface portion 306 extend to be closer to the proximal end side than the middle position H in the central axis direction A of the blade surface region T.

Here, FIG. 19(*a*) illustrates a first virtual plane E1 including the third blade surface portion 307 of the puncture needle 301 by a one-dot chain line. Further, FIG. 19(*b*) illustrates a second virtual plane E2 including a single first connecting blade surface portion 315*a* of the puncture needle 301 by a two-dot chain line. Further, FIG. 19(*c*) illustrates a third virtual plane E3 including the second blade surface portion 306 of the puncture needle 301 by a broken line. Further, FIG. 19(*d*) illustrates a relation among the first virtual plane E1, the second virtual plane E2 and the third virtual plane E3 in a cross-section (the XXVI-XXVI cross-section of FIGS.

19(a) to 19(c)) orthogonal to the central axis direction A at the position where the blade edge 309 is formed.

As illustrated in FIG. 19(d), in the XXVI-XXVI cross-section of FIGS. 19(a) to 19(c), when compared at the position of the second blade surface portion 306 in the third virtual plane E3, the second virtual plane E2 is located between the first virtual plane E1 and the third virtual plane E3. That is, in the cross-sectional view of FIG. 19(d), the second virtual plane E2 is located between the first virtual plane E1 and the second blade surface portion 306. In other words, the portion of the puncture needle 301 in which the blade edge 309 is formed does not intersect with the first virtual plane E1 and the second virtual plane E2, and is located on one side across the first virtual plane E1 and the second virtual plane E2. This is because, in the method for manufacturing the puncture needle 301 to be described later, when the first connecting blade surface portion 315a is formed, the position of the original shape blade surface portion 60 (see FIGS. 18(a) to 18(k)) at which the second blade surface portion 306 is formed is simultaneously ground (see FIGS. 18(d) to 18(f) and the like).

Although the second virtual plane E2 is a plane including the first connecting blade surface portion 315a closest to the proximal end side, even when another plane including the other first connecting blade surface portion 315a is set as the second virtual plane E2, the above-mentioned relation among the first virtual plane E1, the second virtual plane E2 and the third virtual plane E3 is established.

The relation among the first virtual plane E1, the second virtual plane E2 and the third virtual plane E3 is also established in three virtual planes, that is, a virtual plane including the third blade surface portion 307, a virtual plane including a single second connecting blade surface portion 315b, and a virtual plane including the first blade surface portion 305.

Furthermore, all of the puncture needles illustrated in FIGS. 1(a) to 10(b) are hollow needles which define the hollow portion, but may be a solid needle as illustrated in FIGS. 11(a) to 11(d).

Figure 10A:
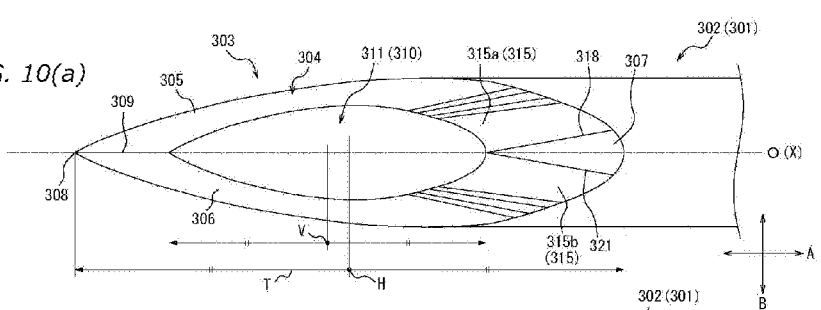
FIG. 10(a) is a plan view of the front side in the vicinity of the distal end portion of the main body portion of the puncture needle as an example of a puncture needle according to the present invention.
Figure 10B:
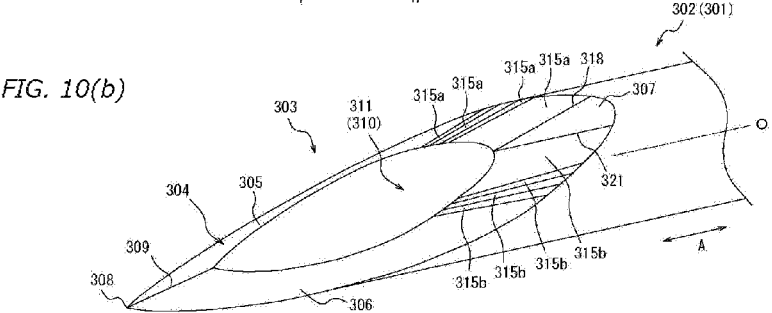
FIG. 10(b) is a perspective view in the vicinity of the distal end portion.
Figure 11A:
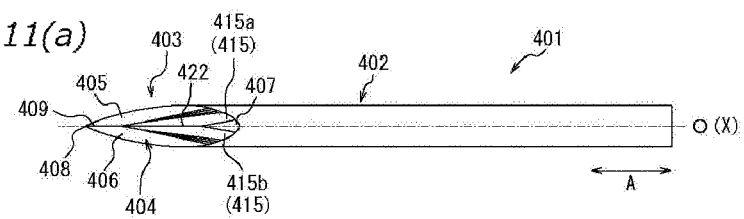
FIGS. 11(a), 11(b), 11(c) and 11(d) are a plan view and a side view of a front side of a puncture needle, and a plan view and a perspective view of a back side thereof, as an embodiment of the present invention, respectively.
Figure 11B:
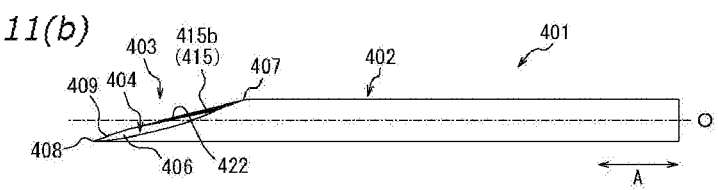
Figure 11C:
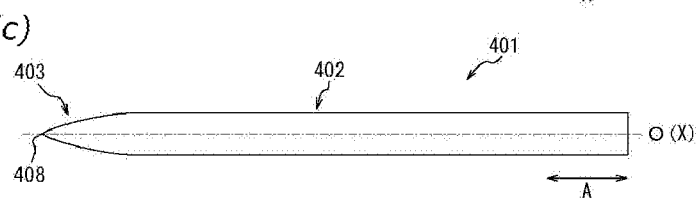
Figure 11D:
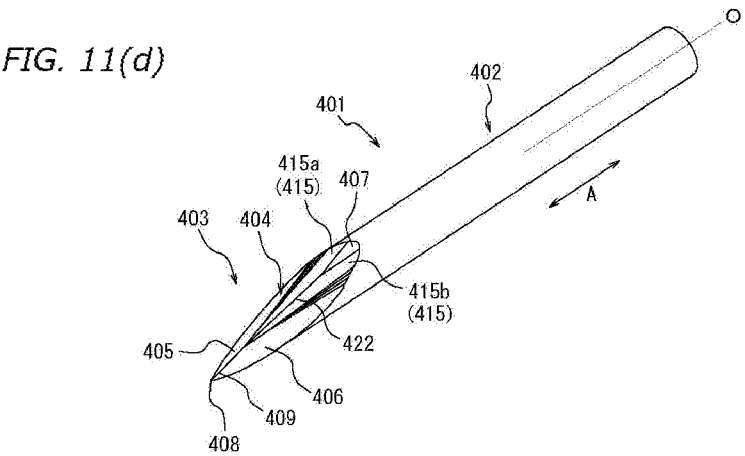
Figure 12A:
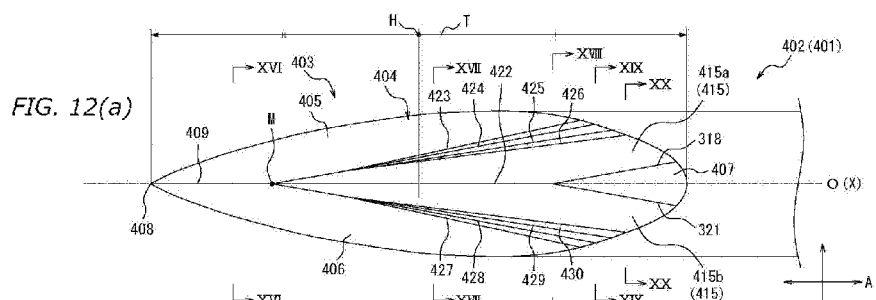
FIGS. 12(a) and 12(b) are enlarged views of the vicinity of the distal end portion of the main body portion of the puncture needle illustrated in FIGS. 11(a) and 11(b), respectively.
Figure 12B:
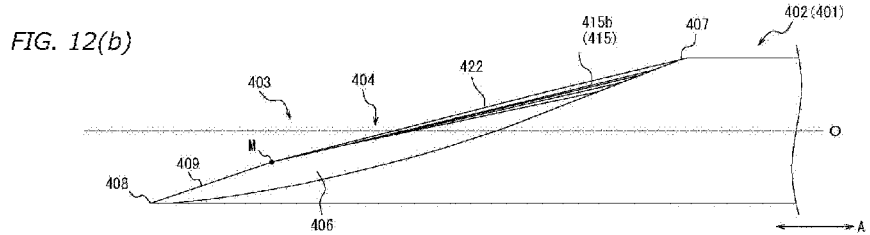
Figure 13A:
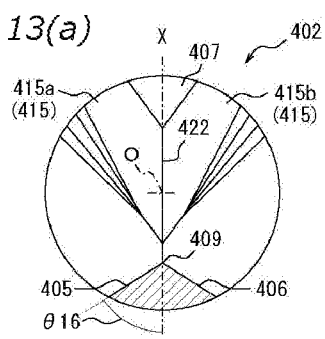
FIGS. 13(a), 13(b), 13(c), 13(d) and 13(e) are cross-sectional views taken along a line XVI-XVI, a line XVII-XVII, a line XVIII-XVIII, a line XIX-XIX and a line XX-XX in FIG. 12(a), respectively.
Figure 13B:
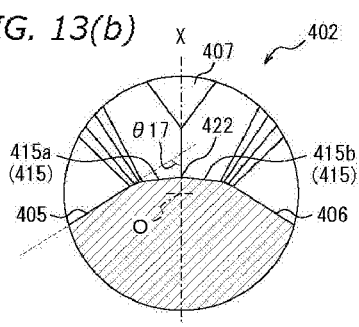
Figure 13C:
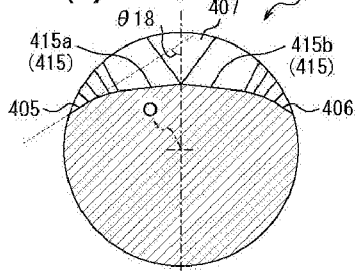
Figure 13D:
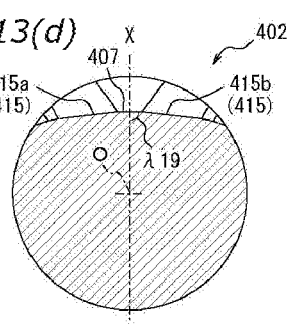
Figure 13E:
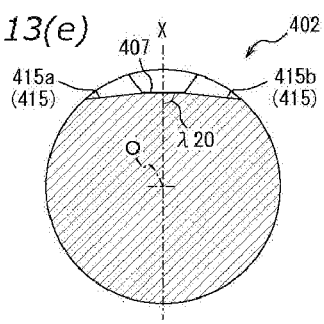

FIGS. 11(a) to 11(d) are views illustrating a solid puncture needle 401 in which the hollow portion 310 of the puncture needle 301 illustrated in FIGS. 10(a) and 10(b) is not formed. Specifically, FIG. 11(a) is a plan view of the front side of the puncture needle 401, FIG. 11(b) is a side view of the puncture needle 401, and FIG. 11(c) is a plan view of the back side of the puncture needle 401. FIG. 11(d) is a perspective view of the puncture needle 401. FIGS. 12(a) and 12(b) are enlarged views of the vicinity of the distal end portion 403 of the main body portion 402 of the puncture needle 401 illustrated in FIGS. 11(a) and 11(b).

The puncture needle 401 illustrated in FIGS. 11(a) to 11(d) and FIGS. 12(a) and 12(b) has a solid rod-shaped main body portion 402 in which a blade surface 404 is formed at the distal end portion 403, and the blade surface 404 has a first blade surface portion 405 and a second blade surface portion 406 which form a blade edge 409 with a needle tip 408 as one end by ridge lines intersecting with each other, on the distal end side. Further, the blade surface 404 has a third blade surface portion 407, which is continuous with the first blade surface portion 405 and the second blade surface portion 406 via a plurality of connecting blade surface portions 415 and is made up of a plane constituting the proximal end of the blade surface 404. The puncture needle 401 illustrated in FIGS. 11(a) to 12(b) is different from the puncture needle 301 illustrated in FIGS. 10(a) and 10(b) described above in that the hollow portion is not defined. Therefore, since the puncture needle 401 has no distal end opening, the shapes of each blade surface portion on the blade surface 404 are different from the shapes of each blade surface portion of the blade surface 304 (see FIGS. 10(a) and 10(b)) of the aforementioned puncture needle 301.

Specifically, since the main body portion 402 of the puncture needle 401 does not define the hollow portion, the plurality of first connecting blade surface portions 415a is continuously disposed in the direction orthogonal to the central axis direction A in the plan views of FIGS. 11(a) and 12(a), and each of the first connecting blade surface portions 415a extends along the central axis O.

Further, in the plan views in FIGS. 11(a) and 12(a), the plurality of second connecting blade surface portions 415b is disposed continuously in a direction orthogonal to the central axis direction A, on the opposite side of the first connecting blade surface portion 415a across the central plane X including the central axis O and the needle tip 408. Each of the second connecting blade surface portions 415b extends along the central axis O.

Further, in the plan views of FIGS. 11(a) and 12(a), the first connecting blade surface portion 415a extending to be closest to the proximal end side among the plurality of first connecting blade surface portions 415a, and the second connecting blade surface portion 415b extending to be closest to the proximal end side among the plurality of second connecting blade surface portions 415b, which are adjacent to each other across the central plane X, form the central ridge portion 422 by the ridge lines intersecting with each other, in the central plane X. The central ridge portion 422 extends from the proximal end of the blade edge 409 to the distal end of the third blade surface portion 407. The shape of the third blade surface portion 407 is similar to the shape of the third blade surface portion 307 of the aforementioned puncture needle 301. Specifically, the third blade surface portion 407 has a substantially fan shape in which an outline is formed by two ridge portions 318 and 321 located between the connecting blade surface portion 415 and the third blade surface portion 407, and a boundary between the outer circumferential surface of the main body portion 402 and the third blade surface portion 407.

Also, among the plurality of first connecting blade surface portions 415a, the first connecting blade surface portions 415a other than the single first connecting blade surface portion 415a forming the central ridge portion 422 extend to converge to the proximal end M of the blade edge 409. Specifically, as illustrated in FIG. 12(a), there are three first connecting blade surface portions 415a other than the single first connecting blade surface portion 415a forming the central ridge portion 422, and between the single first connecting blade surface portion 415a forming the central ridge portion 422 and the first blade surface portion 405, four ridge lines (the first ridge portion 423, the second ridge portion 424, the third ridge portion 425, and the fourth ridge portion 426) formed by the three first connecting blade surface portions 415a extend along the central axis O, and converge to a single point at the proximal end M of the blade edge 409. In other words, the first connecting blade surface portions 415a other than the single first connecting blade surface portion 415a forming the central ridge portion 422 have an elongated shape extending along the central axis O in the plan views of FIGS. 11(a) and 12(a), and have a shape in which the width in the direction orthogonal to the extending direction gradually increases toward the proximal end side of the central axis direction A in the extending direction.

Further, among the plurality of second connecting blade surface portions 415b, the second connecting blade surface portions 415b other than the single second connecting blade surface portion 415b forming the central ridge portion 422 also extend to converge to the proximal end M of the blade edge 409. Specifically, as illustrated in FIGS. 12(a) and 12(b), there are three second connecting blade surface portions 415b other than the single second connecting blade surface portion 415b forming the central ridge portion 422, and between the single second connecting blade surface portion 415b forming the central ridge portion 422 and the second blade surface portion 406, four ridge lines (the fifth ridge portion 427, the sixth ridge portion 428, the seventh ridge portion 429, and the eighth ridge portion 430) formed by the three second connecting blade surface portions 415b extend along the central axis O, and converge to a single point at the proximal end M of the blade edge 409. In other words, the second connecting blade surface portions 415b other than the single second connecting blade surface portion 415b forming the central ridge portion 422 have an elongated shape extending along the central axis O in the plan views of FIGS. 11(a) and 12(a), and have a shape in which the width in the direction orthogonal to the extending direction gradually increases toward the proximal end side of the central axis direction A in the extending direction.

Further, in the solid puncture needle 401 illustrated in FIGS. 11(a) to 11(d) and FIGS. 12(a) and 12(b), as in the puncture needle illustrated in FIGS. 1(a) to 10(b), the first blade surface portion 405 and the second blade surface portion 406 also extend to be closer to the proximal end side of the main body portion 402 than the middle position H in the central axis direction A of the blade surface region T in which the blade surface 404 is formed.

FIGS. 13(a), 13(b), 13(c), 13(d) and 13(e) are cross-sectional views taken along a line XVI-XVI, a line XVII-XVII, a line XVIII-XVIII, a line XIX-XIX and a line XX-XX in FIG. 12(a), respectively. The first blade surface portion 405 and the second blade surface portion 406 (see FIGS. 13(a) to 13(c)) inclined at angles θ16 to θ18 (θ16 to θ18 are equal to one another) with respect to the central plane X are smoothly connected, by the third blade surface portion 407 (see FIGS. 13(d) and 13(e)) extending at angles λ19 and λ20 (λ19 and λ20 are equal to each other at about 90 degrees) with respect to the central plane X, and the plurality of first connecting blade surface portions 415a and the plurality of second connecting blade surface portions 415b made up of a plane (see FIGS. 13(b) to 13(e)).

In the solid puncture needle 401 illustrated in FIGS. 11(a) to 13(e), the first blade surface portion 405, the second blade surface portion 406, the respective connecting blade surface portions 415, and the third blade surface portion 407 are made up of a plane, and at least one connecting blade surface portion 415 may be a curved blade surface portion made up of a curved surface. Further, the third blade surface portion 407 may be made up of a curved surface.

Furthermore, the main body portion of the puncture needle illustrated in FIGS. 1(a) to 13(e) has a sectional outer shape with a substantially circular cross-section at an arbitrary position in the central axis direction A, but a hollow rod-like or solid rod-like main body portion may be adopted, and the present invention is not limited to this configuration. Therefore, for example, a main body portion having a sectional outer shape with a substantially elliptical cross-section at an arbitrary position in the central axis direction A may be adopted. Further, depending on the position in the central axis direction A, a main body portion having both of a portion having a substantially circular cross-sectional outer shape and a portion having a substantially elliptical cross-sectional outer shape may be adopted. Furthermore, a main body portion partially having a portion having a substantially circular sectional outer shape or a substantially elliptical sectional outer shape may be adopted. Further, the shape other than the circular shape may be any shape having a flat sectional outer shape in which a major axis and a minor axis are defined, and is not limited to the aforementioned elliptical shape. Therefore, for example, a round-cornered rectangular sectional outer shape in which a semicircle is combined with both ends of a short side of a rectangle may be adopted.

Figure 14A:
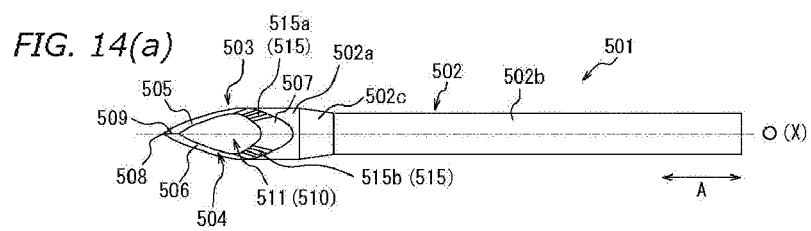
FIGS. 14(a), 14(b), 14(c), and 14(d) are a plan view and a side view of a front side of a puncture needle, and a plan view and a perspective view of a back side thereof, as an embodiment of the present invention, respectively.
Figure 14B:
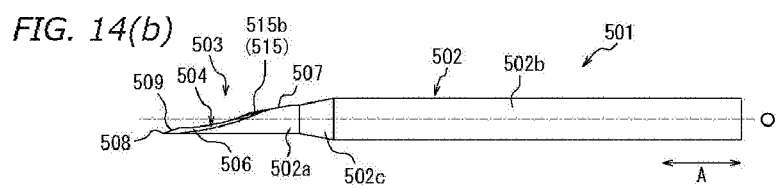
Figure 14C:
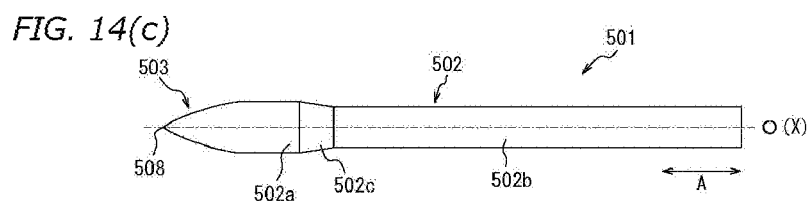
Figure 14D:
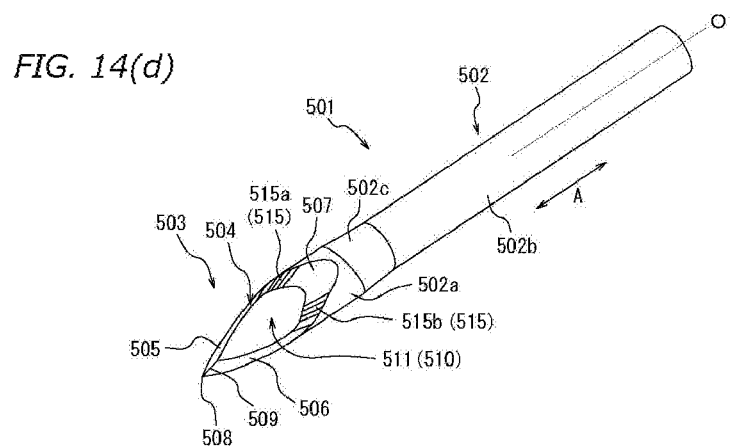

FIGS. 14(a) to 14(d) and FIGS. 15(a) and 15(b) are views illustrating a puncture needle 501 including a main body portion 502 in which an arbitrary cross-sectional outer shape is a substantially circular shape or a substantially elliptical shape. Specifically, FIG. 14(a) is a plan view of the front side of the puncture needle 501, FIG. 14(b) is a side view of the puncture needle 501, and FIG. 14(c) is a plan view of the back side of the puncture needle 501. FIG. 14(d) is a perspective view of the puncture needle 501. FIGS. 15(a) and 15(b) are enlarged views of the vicinity of the distal end portion 503 of the main body portion 502 of the puncture needle 501 illustrated in FIGS. 14(a) and 14(b).

The puncture needle 501 illustrated in FIGS. 14(a) to 14(d) and FIGS. 15(a) and 15(b) includes a main body portion 502 in which a blade surface 504 is formed at a distal end portion 503. The main body portion 502 is a hollow rod-shaped body, that is, a tubular tube body, and defines a hollow portion 510 which communicates from the proximal end to the distal end. A distal end opening 511, which is one end on the distal end side of the hollow portion 510, is defined by the inner edge of the blade surface 504 formed at the distal end portion 503.

The blade surface 504 has a first blade surface portion 505 and a second blade surface portion 506 which form a blade edge 509 with a needle tip 508 as one end by ridge lines intersecting with each other, on the distal end side. The blade surface 504 has a third blade surface portion 507, which is continuous with the first blade surface portion 505 and the second blade surface portion 506 via a plurality of connecting blade surface portions 515, and is made up of a plane forming the proximal end of the blade surface 504. The plurality of connecting blade surface portions 515 includes a plurality of first connecting blade surface portions 515a which connects the first blade surface portion 505 and the third blade surface portion 507, and a plurality of second connecting blade surface portions 515b which connects the second blade surface portion 506 and the third blade surface portion 507.

The puncture needle 501 illustrated in FIGS. 14(a) to 14(d) and FIGS. 15(a) and 15(b) is different from the puncture needle 101 according to the second embodiment described above in sectional outer shape of the main body portion, and other configurations are similar. Hereinafter, this difference will be mainly described.

The main body portion 502 of the puncture needle 501 has a substantially elliptical sectional outer shape, and includes a distal end side main body portion 502a including a distal end portion 503, a proximal end side main body portion 502b which is located on the proximal end side of the distal end side main body portion 502a and has a substantially circular sectional outer shape, and a connecting portion 502c which is located between the distal end side main body portion 502a and the proximal end side main body portion 502b to connect the distal end side main body portion 502a and the proximal end side main body portion 502b. Here, the term "sectional outer shape" used herein means an outer shape in a cross-section orthogonal to the central axis O of the main body portion 502, similarly to the aforementioned embodiment.

The distal end side main body portion 502a has a substantially elliptical sectional outer shape in which a width S1 in the plan view of FIG. 15(a) is a major axis and a width S2 in the side view of FIG. 15(b) is a minor axis. As illustrated in FIGS. 15(a) and 15(b), the width S1 serving as the major axis of the distal end side main body portion 502a is larger than an outer diameter of the proximal end side main body portion 502b, and the width S2 serving as the minor axis of the distal end side main body portion 502a is smaller than the outer diameter of the proximal end side main body portion 502b. Further, the central axis of the distal end side main body portion 502a substantially coincides with the central axis of the proximal end side main body portion 502b, and the central axis O of the main body portion 502 is a substantially straight line. Therefore, the connecting portion 502c has a tapered shape that gradually increases toward the distal end side in the central axis direction A in the plan view of the front side and the back side (see FIGS. 14(a), 14(c) and 15(a)), but gradually decreases toward the distal end side in the central axis direction A in the side view (see FIGS. 14(b) and 15(b)). The central plane X including the central axis O and the needle tip 508 is a plane which includes a minor axis in a cross-section orthogonal to the central axis direction A of the distal end side main body portion 502a.

As illustrated in FIGS. 14(a) to 14(d) and FIGS. 15(a) and 15(b), the blade surface 504 is formed in the distal end side main body portion 502a having an approximately elliptical sectional outer shape. The first blade surface portion 505, the second blade surface portion 506 and the connecting blade surface portion 515 of the blade surface 504 are located symmetrically across the central plane X including the minor axis. Further, the first blade surface portion 505, the second blade surface portion 506, the connecting blade surface portion 515 and the third blade surface portion 507 are made up of a plane, and the shapes thereof are the same as those of the first blade surface portion 5, the second blade surface portion 6, the connecting blade surface portion 15 and the third blade surface portion 7 in the puncture needle 1 of the aforementioned first embodiment, or those of the first blade surface portion 105, the second blade surface portion 106, the connecting blade surface portion 115 and the third blade surface portion 107 in the puncture needle 101 of the aforementioned second embodiment. Thus, the description thereof will not be provided here.

In the puncture needle 501 illustrated in FIGS. 14(a) to 14(d) and FIGS. 15(a) and 15(b), like the puncture needle illustrated in FIGS. 1(a) to 13(e), the first blade surface portion 505 and the second blade surface portion 506 also extend to be closer to the proximal end side of the main body portion 502 than the middle position H in the central axis direction A of the blade surface region T in which the blade surface 504 is formed (see FIGS. 15(a) and 15(b)). Further, in the side view of the puncture needle 501 illustrated in FIGS. 14(b) and 15(b), the inner edge of the blade surface 504 includes a curved portion which extends to be curved in a concave shape from one end of the needle tip 508 side (which is the same as the distal end side in the central axis direction A) of the inner edge, in other words, the proximal end of the blade edge 509. Specifically, as illustrated in FIGS. 15(a) and 15(b), the inner edge of the blade surface 504 includes two curved portions, that is, a first curved portion 513a made up of the inner edge of the first blade surface portion 505 and the inner edges of the plurality of first connecting blade surface portions 515a, and a second curved portion 513b made up of the inner edge of the second blade surface portion 506 and the inner edges of the plurality of second connecting blade surface portions 515b. In the side views of FIGS. 14(b) and 15(b), only the second curved portion 513b is in a visible state. As illustrated in FIG. 15(a), the first curved portion 513a and the second curved portion 513b extend to be closer to the proximal end side of the main body portion 502 than the middle position V of the inner edge of the blade surface 504 in the central axis direction A.

In this way, the puncture needle 501 illustrated in FIGS. 14(a) to 14(d) and FIGS. 15(a) and 15(b) differs from the aforementioned hollow puncture needles 1, 101, 201 and 301 in the cross-sectional outer shape at the distal end portion 503 of the main body portion 502. However, even with such a configuration, like the aforementioned hollow puncture needles 1, 101, 201, and 301, it is possible to achieve a blade surface shape with a small blade tip angle α. Further, in the side view (see FIGS. 14(b) and 15(b)), by the configuration in which the curved portion of the inner edge of the blade surface 504 extends to be closer to the proximal end side than the middle position V, it is possible to achieve a blade surface shape having a small blade tip angle α, while reducing the thickness between the blade surface 504 and the back surface of the blade surface 504 as a whole in the side view.

FIGS. 16(a), 16(b), 16(c), 16(d) and 16(e) are cross-sectional views taken along a line XXI-XXI, a line XXII-XXII, a line XXIII-XXIII, a line XXIV-XXIV, and XXV-XXV of FIG. 15(a), respectively. In the cross-sectional views illustrated in FIGS. 16(a) to 16(e), angles θ21 to θ23 of the first blade surface portion 505 and the second blade surface portion 506 with respect to the central plane X are equal angles, angles λ24 and λ25 of the third blade surface portion 507 with respect to the central plane X are both equal angles at about 90 degrees. As illustrated in FIGS. 16(c) and 16(d), the first blade surface portion 505 and the third blade surface portion 507 are smoothly connected to each other by the four first connecting blade surface portions 515a so as not to form a ridge line which serves as a large step. Similarly, the second blade surface portion 506 and the third blade surface portion 507 are smoothly connected to each other by the four second connecting blade surface portions 515b so as not to form a ridge line which serves as a large step. In FIGS. 16(a) to 16(e), the ridge lines between the blade surface portions are indicated by a solid line.

In the hollow puncture needle illustrated in FIGS. 5(a) to 10(b) and FIGS. 14(a) to 16(e), similarly to the aforementioned puncture needle 1 illustrated in FIGS. 1(a) to 4, the proximal end of the inner edge of the blade surface is provided in the inner edge of the third blade surface portion. Further, the inner edge of the blade surface 4 extends from the distal end side toward the proximal end side of the main body portion 2, in the range from the distal end to the proximal end thereof. More specifically, among the two points in which the inner edges of the blade surface intersect with the central plane X, the point on the distal end side of the main body portion is the distal end of the inner edge of the blade surface, and the point on the proximal end side of the main body portion is the proximal end of the inner edge of the blade surface. Further, the inner edge of the blade surface always extends from the distal end side toward the proximal end side of the main body portion, in the range from the distal end to the proximal end of the inner edge of the blade surface. Further, the distal end opening of the hollow puncture needle illustrated in FIGS. 5(a) to 10(b) and FIGS. 14(a) to 16(e) also has a teardrop shape in the front view, like the distal end opening 11 of the puncture needle 1 illustrated in FIGS. 1(a) to 4.

Third Embodiment

Figure 17:
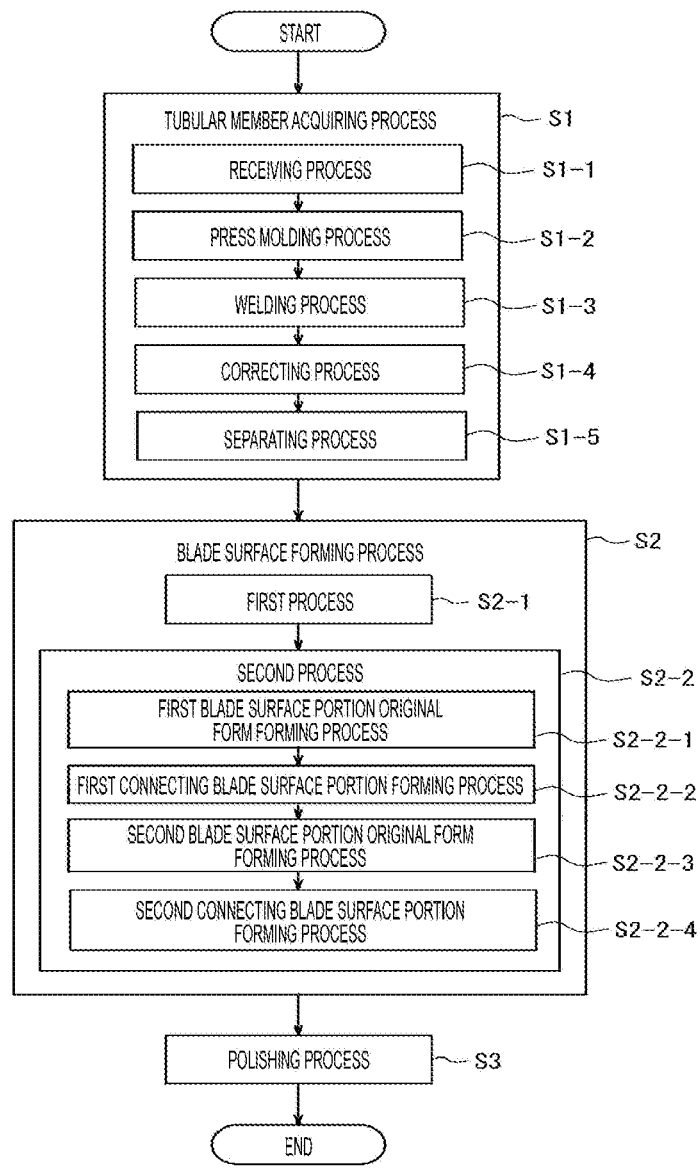
FIG. 17 is a flowchart illustrating a method for manufacturing the puncture needle illustrated in FIGS. 10(a) and 10(b).

Next, a method for manufacturing the puncture needle 301 (see FIGS. 10(a) and 10(b)) as an embodiment of the present invention will be described. FIG. 17 is a flowchart illustrating a method for manufacturing the puncture needle 301. As illustrated in FIG. 17, the method for manufacturing the puncture needle 301 includes a tubular member obtaining step S1 of obtaining a tubular member which is in a state prior to cutting of the puncture needle 301, a blade surface forming step S2 of forming a blade surface in at least one end portion of the tubular member, and a polishing step S3 of polishing the tubular member having the blade surface formed thereon, using various polishing treatments such as electrolytic polishing treatment.

The tubular member obtaining step S1 can be performed by various known methods, and includes, for example, a receiving step S1-1 of receiving a strip-like metallic plate material into a press molding machine, a press molding step S1-2 of performing continuous press molding on the plate material using the press molding machine to obtain a plurality of tube bodies in a state of being partially connected to the plate material, a joining step S1-3 of bonding a joint portion of the tube body with welding or an adhesive, a correction step S1-4 of correcting the shape of the tube body so that the central axis of the tube body is a substantially straight line, and a separation step S1-5 of separating the tube body from the plate material to obtain a tubular member 70 that is in a state prior to cutting of the puncture needle 301.

FIGS. 18(a) to 18(k) are schematic diagrams illustrating the outline of the blade surface forming step S2. Specifically, FIGS. 18(a) to 18(k) illustrate a process in which each blade surface portion is successively formed in the blade surface forming step S2.

The blade surface forming step S2 includes a first step S2-1 of creating an original shape blade surface portion 60 inclined with respect to the central axis direction Y at one end portion of the tubular member 70 obtained in the tubular member obtaining step S1, and a second step S2-2 of creating the first blade surface portion 305 (see FIGS. 10(a) and 10(b)) and the second blade surface portion 306 (see FIGS. 10(a) and 10(b)) which form the blade edge 309 (see FIGS. 10(a) and 10(b)) with the needle tip 308 (see FIGS. 10(a) and 10(b)) as one end by the ridge lines intersecting with each other, by grinding apart of the distal end side of the original shape blade surface portion 60 formed in the first step S2-1 with a wire cut, a whetstone or the like.

Further, in the second step S2-2, at least one blade surface portion of the first blade surface portion 305 and the second blade surface portion 306 is formed by a plane which extends to be closer to the other end portion side of the tubular member 70 than the middle position in the central axis direction Y of the original shape blade surface region in which the original shape blade surface portion 60 is formed. In this manner, like the puncture needle 301, it is easy to achieve a configuration in which at least one of the first blade surface portion 305 and the second blade surface portion 306 extends to be closer to the proximal end side than the middle position H (see FIGS. 10(a) and 10(b)) in the central axis direction A of the blade surface region T (see FIGS. 10(a) and 10(b)). As a result, it is easy to achieve the puncture needle 301 having a small blade tip angle α (see FIG. 2(b)).

Furthermore, it is easy to achieve a configuration in which the inner edge of the blade surface 304 has a curved portion that extends to be curved in a concave shape from one end on the needle tip 308 side of the inner edge, in other words, the proximal end of the blade edge 309 in a side view. As a result, it is easy to achieve the puncture needle 301 that suppresses winding of the edge portion of the incision of the body surface at the time of puncturing and reduces the risk of infection caused by saprophytic bacteria or the like. Further, it is easy to achieve the puncture needle 301 which has a thin blade surface 304 and a small blade tip angle α.

Hereinafter, the details of the blade surface forming step S2 will be described.

Figures 18A, 18B, 18C, 18D, 18E, 18F:
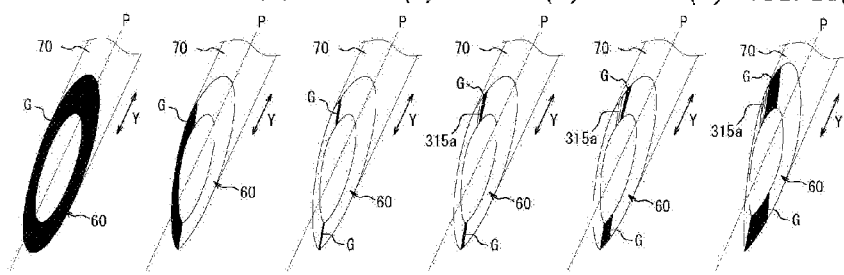
FIGS. 18(a) to 18(k) are schematic diagrams illustrating an outline of a blade surface forming process in FIG. 17.

FIG. 18(a) illustrates the first step S2-1 of the blade surface forming step S2. As illustrated in FIG. 18(a), in the first step S2-1 of the blade surface forming step S2, by a wire cutting process or a grinding process using a whetstone, an original shape blade surface portion 60 inclined with respect to the central axis direction Y of the tubular member 70 is formed. Specifically, in the first step S2-1 of the present embodiment, by a grinding process with a whetstone at the end portion of the tubular member 70, a planar inclined surface as the original shape blade surface portion 60 which is inclined with respect to the central axis P of the tubular member 70 is formed. In the present embodiment, the tubular member 70 is not rotated, and the end portion of the tubular member 70 is brought into sliding contact with the grinding surface of the whetstone in a state where the inclination angle of the central axis P of the tubular member 70 with respect to the grinding surface of the whetstone is kept constant, thereby forming the original shape blade surface portion 60. However, the original shape blade surface portion 60 may be formed in the press molding step S1-2 in the aforementioned tubular member obtaining step S1.

In FIG. 18(a), the grinding surface G of the tubular member 70, which is included in a substantially single plane that can be ground simultaneously by the grinding surface of the rotating whetstone and is simultaneously ground by the grinding surface, is expressed by being filled with color. Expression of the grinding surface G is also similar in FIGS. 18(b) to 18(k) referred to below.

FIGS. 18(b) to 18(k) illustrate the second step S2-2 of the blade surface forming step S2.

The second step S2-2 of the blade surface forming step S2 includes a first blade surface portion original shape forming step S2-2-1 of forming the original shape of the first blade surface portion 305, a first connecting blade surface portion forming step S2-2-2 of forming the plurality of first connecting blade surface portions 315a (see FIGS. 10(a) and 10(b)), a second blade surface portion original shape forming step S2-2-3 of forming the original shape of the second blade surface portion 306 and forming the first blade surface portion 305, and a second connecting blade surface portion forming step S2-2-4 of forming a plurality of second connecting blade surface portions 315b (see FIGS. 10(a) and 10(b)) and forming the second blade surface portion 306.

FIG. 18(b) illustrates the first blade surface portion original shape forming step S2-2-1 of forming the original shape of the first blade surface portion 305. As illustrated in FIG. 18(b), the original shape of the first blade surface portion 305 is formed by grinding a part of the distal end side of the original shape blade surface portion 60.

When forming the original shape of the first blade surface portion 305 in FIG. 18(b), in a state in which the inclination angle, at which the central axis P of the tubular member 70 is inclined with respect to the grinding surface of the whetstone, is set to a predetermined angle, grinding is performed by bringing the original shape blade surface portion 60 located at one end portion of the tubular member 70 into sliding contact with the grinding surface of the whetstone which rotates at high speed.

FIGS. 18(c) to 18(f) illustrate the first connecting blade surface portion forming step S2-2-2 of forming a plurality of first connecting blade surface portions 315a. The tubular member 70 illustrated in FIG. 18(c) is rotated around the central axis P from the tubular member 70 illustrated in FIG. 18(b) by a predetermined angle, and the inclination angle between the central axis P and the grinding surface of the whetstone is in a state of being varied. Further, the tubular member 70 illustrated in FIG. 18(d) is further rotated around the central axis P from the tubular member 70 illustrated in FIG. 18(c) by a predetermined angle in the same direction, and inclination angle between the central axis P and the grinding surface of the whetstone is in a state of being further varied in the same direction. By sequentially rotating the tubular member 70 about the central axis and varying the inclination angle of the tubular member 70 in this manner, the grinding location of the tubular member 70 is sequentially moved, and as illustrated in FIGS. 18(c) to 18(f), a plurality of first connecting blade surface portions 315a is formed.

Further, as illustrated in FIGS. 18(c) to 18(f), when forming the first connecting blade surface portion 315a, in the original shape blade surface portion 60, a portion to be ground when the second blade surface portion 306 is formed in a later step is simultaneously ground.

Further, after the first connecting blade surface portion forming step S2-2-2, the tubular member 70 is reset to the position and attitude for starting the second blade surface portion original shape forming step S2-2-3, and the second blade surface portion original shape forming step S2-2-3 can be started after the reset is completed.

Figures 18G, 18H, 18I, 18J, 18K:
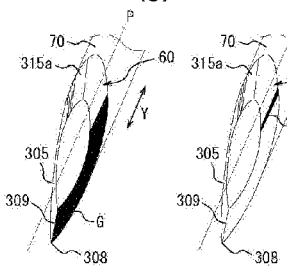

FIG. 18(g) illustrates the second blade surface portion original shape forming step S2-2-3 of forming the original shape of the second blade surface portion 306 and forming the first blade surface portion 305. As illustrated in FIG. 18(g), the original shape of the second blade surface portion 306 is formed, by grinding a part of the distal end side of the original shape blade surface portion 60, at a position opposite to the position where the original shape of the first blade surface portion 305 is formed across the distal end opening 311 (see FIGS. 10(a) and 10(b)). When forming the original shape of the second blade surface portion 306 in FIG. 18(g), in a state in which the inclination angle, at which the central axis P of the tubular member 70 is inclined with respect to the grinding surface of the whetstone, is set to a predetermined angle, grinding is performed by bringing the original shape blade surface portion 60 located at one end portion of the member 70 into sliding contact with the grinding surface of the whetstone which rotates at high speed.

Further, when forming the original shape of the second blade surface portion 306, a ridge line intersecting with the original shape of the first blade surface portion 305 is formed on the distal end side of the original shape of the second blade surface portion 306. This ridge line is a blade edge 309 with the needle tip 308 as one end. That is, the blade edge 309 is formed by forming the original shape of the second blade surface portion 306, and as a result, the outline of the first blade surface portion 305 is determined. That is, the first blade surface portion 305 is formed.

FIGS. 18(h) to 18(k) illustrate the second connecting blade surface portion forming step S2-2-4 of forming a plurality of second connecting blade surface portions 315b and forming the second blade surface portion 306. The tubular member 70 illustrated in FIG. 18(h) is rotated around the central axis P from the tubular member 70 illustrated in FIG. 18(g) by a predetermined angle, and the inclination angle between the central axis P and the grinding surface of the whetstone is in a state of being varied. The rotation direction is opposite to the rotation direction when the tubular member 70 is sequentially changed from the state illustrated in FIG. 18(b) to the state illustrated in FIG. 18(f).

Further, the tubular member 70 illustrated in FIG. 18(i) is further rotated around the central axis P from the tubular member 70 illustrated in FIG. 18(h) by a predetermined angle in the same direction, and the inclination angle between the central axis P and the grinding surface of the whetstone is in the state of being further varied in the same direction. By sequentially rotating the tubular member 70 about the central axis and varying the inclination angle of the tubular member 70 in this manner, the grinding location of the tubular member 70 is sequentially moved, and as illustrated in FIGS. 18(h) to 18(k), a plurality of second connecting blade surface portions 315b is formed.

Further, in the second connecting blade surface portion forming step S2-2-4, by forming the second connecting blade surface portion 315b, a ridge line is formed between the original shape of the second blade surface portion 306 and the second connecting blade surface portion 315b. That is, the outline of the second blade surface portion 306 is defined by forming the second connecting blade surface portion 315b. That is, the second blade surface portion 306 is formed.

As a result of forming all the second connecting blade surface portions 315b, the remaining portion of the original shape blade surface portion 60 serves as the third blade surface portion 307. In other words, the third blade surface portion 307 is made up of a part of the original shape blade surface portion 60.

In this way, in the second step S2-2 of the blade surface forming step S2, the blade surface 304 of the puncture needle 301 is formed, by performing the first blade surface portion original shape forming step S2-2-1, the first connecting blade surface portion forming step S2-2-2, the second blade surface portion original shape forming process S2-2-3 and the second connecting blade surface portion forming step S2-2-4.

In order to change the state of the tubular member 70 from the state illustrated in FIG. 18(b) to the state illustrated in FIG. 18(f), the tubular member 70 rotates around the central axis a plurality of times (four times in the present embodiment). However, the angular change amounts in each of the multiple rotations can be made approximately equal to each other. The same also applies to the case of changing the tubular member 70 from the state illustrated in FIG. 18(g) to the state illustrated in FIG. 18(k).

Here, in the blade surface forming step S2 of the present embodiment, by performing the first connecting blade surface portion forming step S2-2-2 and the second connecting blade surface portion forming step S2-2-4, the third blade surface portion 307, the first connecting blade surface portion 315a and the second connecting blade surface portion 315b made up of a part of the original shape blade surface portion 60 is formed. Further, when forming the first connecting blade surface portion 315a and the second connecting blade surface portion 315b, the ridge portion 318 (see FIGS. 10(a) and 10(b)) formed by the ridge line in which the third blade surface portion 307 and the first connecting blade surface portion 315a intersect with each other, and the ridge portion 321 (see FIGS. 10(a) and 10(b)) formed by the ridge line in which the third blade surface portion 307 and the second connecting blade surface portion 315b intersect with each other are formed to extend along the central axis P. Furthermore, one end of the other end portion side (which is the same as the proximal end side of the puncture needle 301) of the tubular member 70 in the ridge portions 318 and 321 is formed to be located between one end on the other end portion side of the tubular member 70 in the inner edge of the original shape blade surface portion 60 and one end on the other end portion side of the tubular member 70 in the outer edge of the original shape blade surface portion 60 in the central axis direction Y. In this way, it is possible to suppress an increase in piercing resistance in the heel portion of the blade surface 304.

Although the method for manufacturing the puncture needle 301 illustrated in FIGS. 10(a) and 10(b) is illustrated in this embodiment, it is also possible to form the blade surface by the same manufacturing method for the puncture needle illustrated in FIGS. 1(a) to 9(e) and FIGS. 11(a) to 16(e). Further, in the present embodiment, although an example in which the blade surface 304 is formed by a grinding process with a whetstone is illustrated, a blade surface may be formed by a wire cutting process. Furthermore, in the puncture needle 301 manufactured by the manufacturing method of the present embodiment, although the first connecting blade surface portion 315a and the second connecting blade surface portion 315b are planar blade surface portions made up of a plane, the first and second connecting blade surface portions 315a and 315b may be curved blade surface portions made up of a curved surface (see FIG. 8 and the like). When forming the first connecting blade surface portion 315a and the second connecting blade surface portion 315b having such a curved surface shape by the aforementioned grinding process, the rotation of the tubular member 70 and the variation of the inclination angle of the tubular member 70 are simultaneously performed, in the state of bringing the grinding surface G of the tubular member 70 into sliding contact with the grinding surface of the rotating whetstone. Thus, it is possible to achieve the first connecting blade surface portion 315a and the second connecting blade surface portion 315b having a curved surface shape.

Further, in the solid puncture needle 401 illustrated in FIGS. 11(a) to 11(d) and FIGS. 12(a) and 12(b), a solid rod-like member is formed by a known solid rod-like member obtaining step of forming a solid rod-like member instead of the aforementioned tubular member obtaining step S1, and the blade surface 404 can be formed on one end portion of the solid rod-like member, by the same method as the aforementioned blade surface forming step S2. Further, in the puncture needle 501 illustrated in FIGS. 14(a) to 14(d) and FIGS. 15(a) and 15(b), the sectional outer shape of the one end portion, in which the blade surface 504 is formed, can be set to a substantially elliptical shape, by pressing one end portion of the cylindrical tubular member, in the tubular member obtaining step S1 or just before the first step S2-1 in the blade surface forming step S2.

Fourth Embodiment

Figure 20A:
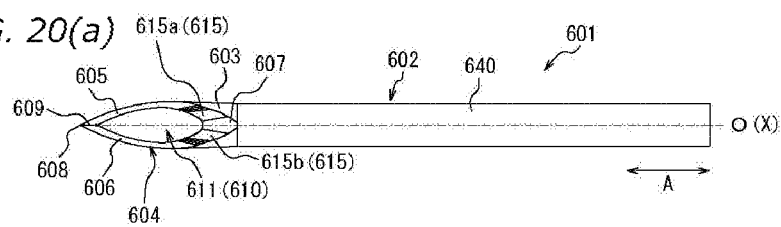
FIGS. 20(a), 20(b), 20(c) and 20(d) are a plan view and a side view of a front side of a puncture needle, and a plan view and a perspective view of a back side thereof, as an embodiment of the present invention, respectively.
Figure 20B:
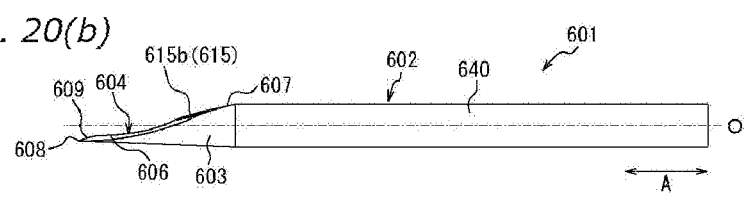
Figure 20C:
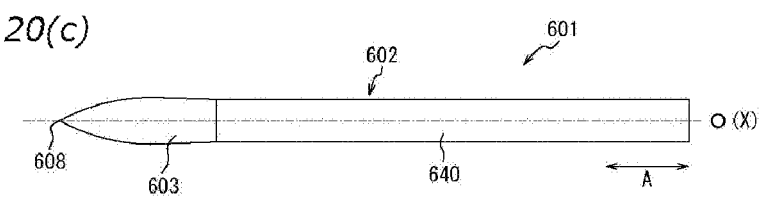
Figure 20D:
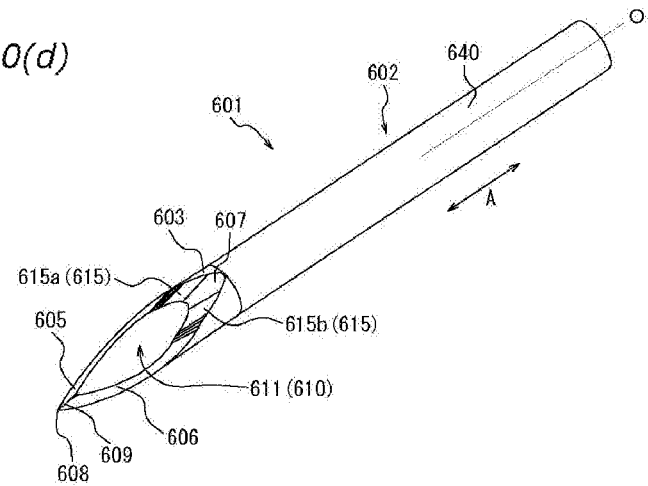
Figure 21A:
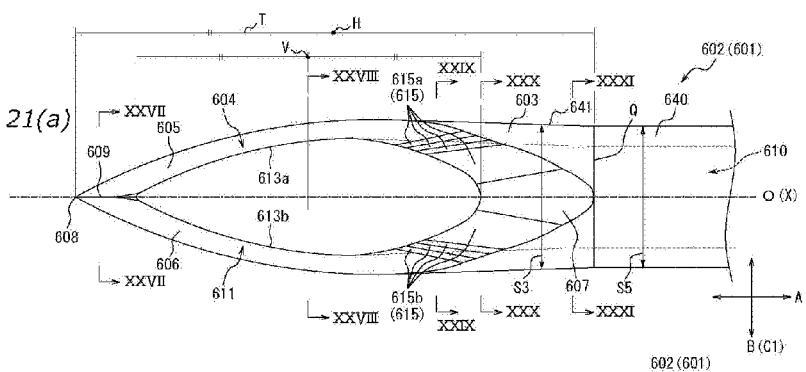
FIGS. 21(a) and 21(b) are enlarged views of the vicinity of the distal end portion of the main body portion of the puncture needle illustrated in FIGS. 20(a) and 20(b), respectively.
Figure 21B:
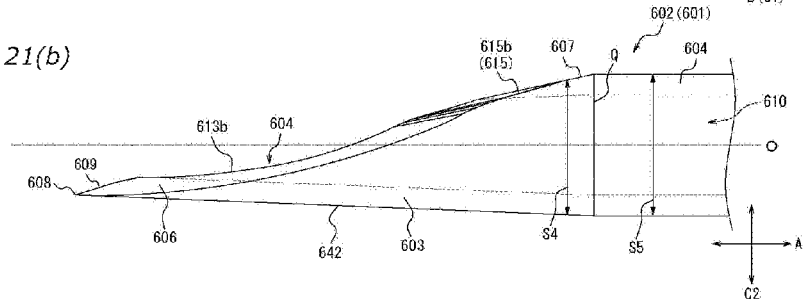

Further, a puncture needle 601 according to another embodiment of the present invention will be described. FIG. 20(a) is a plan view of the front side of the puncture needle 601, FIG. 20(b) is a side view of the puncture needle 601, and FIG. 20(c) is a plan view of the back side (rear side) of the puncture needle 601. FIG. 20(d) is a perspective view of the puncture needle 601. Further, FIGS. 21(a) and 21(b) are enlarged views of the vicinity of the distal end portion 603 of the main body portion 602 of the puncture needle 601 illustrated in FIGS. 20(a) and 20(b) respectively.

A main body portion 602 of the puncture needle 601 illustrated in FIGS. 20(a) to 20(d) and FIGS. 21(a) and 21(b) has a distal end portion 603 having a flat cross-sectional outer shape. The outer shape of the cross-section on the side closer to the proximal end than the distal end portion 603 of the main body portion 602 is substantially circular. Hereinafter, for the sake of convenience of the description, a portion of the main body portion 602 in which the sectional outer shape is substantially circular on the side closer to the proximal end than the flat distal end portion 603 is referred to as "needle stem portion 640".

The puncture needle 601 illustrated in FIGS. 20(a) to 20(d) and FIGS. 21(a) and 21(b) includes the main body portion 602 in which the blade surface 604 is formed at the distal end portion 603. The main body portion 602 is a hollow rod-like tube body, that is, a tubular tube body, and defines a hollow portion 610 which communicates from the proximal end to the distal end. A distal end opening 611, which is one end on the distal end side of the hollow portion 610, is defined by the inner edge of the blade surface 604 formed at the distal end portion 603.

The blade surface 604 has a first blade surface portion 605 and a second blade surface portion 606 which form a blade edge 609 with a needle tip 608 as one end by ridge lines intersecting with each other, on the distal end side. The blade surface 604 has a third blade surface portion 607 that is continuous with the first blade surface portion 605 and the second blade surface portion 606 via a plurality of connecting blade surface portions 615 and is made up of a plane constituting the proximal end of the blade surface 604. The plurality of connecting blade surface portions 615 includes a plurality of first connecting blade surface portions 615a which connects the first blade surface portion 605 and the third blade surface portion 607, and a plurality of second connecting blade surface portions 615b which connects the second blade surface portion 606 and the third blade surface portion 607.

The puncture needle 601 illustrated in FIGS. 20(a) to 20(d) and FIGS. 21(a) and 21(b) differs from the puncture needle 501 illustrated in FIGS. 14(a) to 16(e) mainly in the sectional outer shape of the main body portion. Hereinafter, the difference will be mainly described.

The main body portion 602 of the puncture needle 601 includes a needle stem portion 640 having a substantially circular sectional outer shape, and a distal end portion 603 which is continuous with one end of the needle stem portion 640 and has a flat sectional outer shape. In FIGS. 21(a) and 21(b), a boundary line between the needle stem portion 640 and the distal end portion 603 is indicated by a solid line Q.

The distal end portion 603 of the puncture needle 601 has a substantially elliptical sectional outer shape in which the width direction (vertical direction in FIG. 21(a)) in the plan view of FIG. 21(a) serves as a major axis direction C1, and the width direction (vertical direction in FIG. 21(b)) in the side views of FIG. 21(b) serves as a minor axis direction C2. Furthermore, the outer circumferential surface of the distal end portion 603 of the puncture needle 601 has a tubular shape in which the length in the major axis direction C1 (which is the same direction as the direction B in FIG. 21(a)) gradually increases and the length in the minor axis direction C2 gradually decreases toward the needle tip 608 side in the central axis direction A. In other words, as illustrated in FIG. 21(a), a width S3 of the distal end portion 603 in the major axis direction C1 becomes wider from the position continuous with the needle stem portion 640 toward the needle tip 608 side in the central axis direction A, and becomes larger than the outer diameter S5 of the needle stem portion 640. Conversely, as illustrated in FIG. 21(b), a width S4 of the distal end portion 603 in the minor axis direction C2 becomes narrower from the position continuous with the needle stem portion 640 toward the needle tip 608 side in the central axis direction A, and becomes smaller than the outer diameter S5 of the needle stem portion 640. The central axis of the distal end portion 603 and the central axis of the needle stem portion 640 substantially coincide with each other. That is, as illustrated in FIGS. 20(a) to 20(d) and FIGS. 21(a) and 21(b), the central axis O of the main body portion 602 extends in a straight line at the positions of the distal end portion 603 and the needle stem portion 640.

More specifically, in the front view (see FIG. 21(a)) of the distal end portion 603 viewed opposite to the minor axis direction C2, the outer circumferential surface of the distal end portion 603 of the puncture needle 601 has a tapered portion 641 in which the width S3 in the major axis direction C1 gradually increases toward the needle tip 608 in the central axis direction A. In the central axis direction A, the width S3 of the tapered portion 641 gradually increases from the position continuous with the needle stem portion 640 toward the needle tip 608 side in the central axis direction A, and continues to gradually increase to a position intersecting with the outer edge of the first blade surface portion 605 and the outer edge of the second blade surface portion 606. Conversely, the width S3 of the distal end portion 603 in the major axis direction C1 is the maximum at the position where the first blade surface portion 605 and the second blade surface portion 606 exist in the central axis direction A, and gradually decreases toward the proximal end side in the central axis direction A.

Therefore, after the outer edge of the first blade surface portion 605 and the outer edge of the second blade surface portion 606 have passed through the skin, it is possible to suppress the outer circumferential surface of the distal end portion 603 from pulling the skin around the puncture hole to be wound into the body from the puncture hole. This makes it possible to reduce the pain that the patient feels when puncturing the puncture needle 601.

Further, in the puncture needle 601, in a side view (see FIG. 21(b)) of the distal end portion 603 viewed opposite to the major axis direction C1, on the outer circumferential surface of the distal end portion 603 located on the back side opposite to the blade surface 604, a back inclined portion 642 is formed which is inclined to be closer to the central axis O toward the needle tip 608 in the central axis direction A.

In this manner, by providing the back inclined portion 642 on the outer circumferential surface on the back side of the blade surface 604, a pressing force directed toward the front side in which the blade surface 604 is formed is applied to the puncture needle 601 during puncturing, from the back side via the back inclined portion 642. Therefore, because at least a part of the pressing force from the front side to the back side via the blade surface 604 is canceled out, in the side view (see FIG. 21(b)), it is possible to improve straightness, as compared with a configuration in which the outer circumferential surface on the back side of the blade surface 604 extends in parallel with the central axis direction A and the back inclined portion 642 of the present embodiment does not exist.

As illustrated in FIGS. 20(a) to 20(d) and FIGS. 21(a) and 21(b), the blade surface 604 is formed at the distal end portion 603, and the first blade surface portion 605, the second blade surface portion 606 and the connecting blade surface portion 615 of the blade surface 604 are located symmetrically across the central plane X. The central plane X including the central axis O and the needle tip 608 in the present embodiment is a plane which includes a minor axis in a cross-section orthogonal to the central axis direction A of the distal end portion 603.

Further, the first blade surface portion 605, the second blade surface portion 606, the connecting blade surface portion 615, and the third blade surface portion 607 are made up of a plane, and because the shapes thereof are the same as those of the first blade surface portion 305, the second blade surface portion 306, the connecting blade surface portion 315 and the third blade surface portion 307 in the aforementioned puncture needle 301 illustrated in FIGS. 10(a) and 10(b), the description thereof will not be provided here.

Here, in the puncture needle 601 illustrated in FIGS. 20(a) to 20(d) and FIGS. 21(a) and 21(b), like the aforementioned puncture needle illustrated in FIGS. 1(a) to 16(e), the first blade surface portion 605 and the second blade surface portion 606 also extend to be closer to the proximal end side of the main body portion 602 than the middle position H in the central axis direction A of the blade surface region T in which the blade surface 604 is formed (see FIGS. 21(a) and 21(b)). Further, the inner edge of the blade surface 604 has a curved portion that extends to be curved in a concave shape from one end of the needle tip 608 side (which is the same as the distal end side in the central axis direction A) of the inner edge, in the side view of the puncture needle 601 illustrated in FIGS. 20(b) and 21(b). Specifically, as illustrated in FIGS. 21(a) and 21(b), the inner edge of the blade surface 604 has two curved portions, that is, a first curved portion 613a which includes the inner edge of the first blade surface portion 605 and the inner edges of the plurality of first connecting blade surface portions 615a, and a second curved portion 613b which includes the inner edge of the second blade surface portion 606 and the inner edges of the plurality of second connecting blade surface portions 615b. In the side views of FIGS. 20(b) and 21(b), only the second curved portion 613b is in a visible state. As illustrated in FIG. 21(a), the first curved portion 613a and the second curved portion 613b extend to be closer to the proximal end side of the main body portion 602 than the middle position V of the inner edge of the blade surface 604 in the central axis direction A.

In this manner, in the puncture needle 601 illustrated in FIGS. 20(a) to 20(d) and FIGS. 21(a) and 21(b), it is possible to achieve a blade surface shape having a small blade tip angle α (see FIG. 2(b)). Further, by a configuration in which the curved portion of the inner edge of the blade surface 604 extends to be closer to the proximal end side than the middle position V in the side view (see FIGS. 20(b) and 21(b)), it is possible to achieve a blade surface shape having a small blade tip angle α (see FIG. 2(b)), while reducing the thickness between the blade surface 604 and the back surface (rear surface) of the blade surface 604 in the side view as a whole.

Figure 22A:
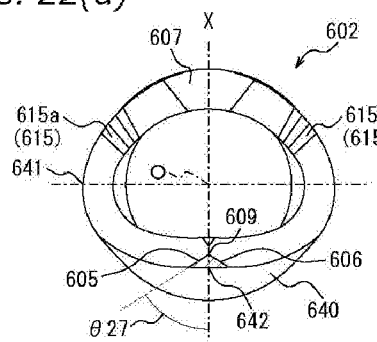
FIGS. 22(a), 22(b), 22(c), 22(d), and 22(e) are cross-sectional views taken along a line XXVII-XXVII, a line XXVIII-XXVIII, a line XXIX-XXIX, a line XXX-XXX, and a line XXXI-XXXI of FIG. 21(a), respectively.
Figure 22B:
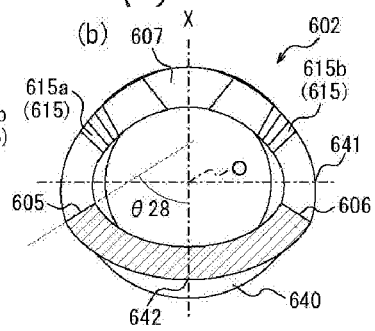
Figure 22C:
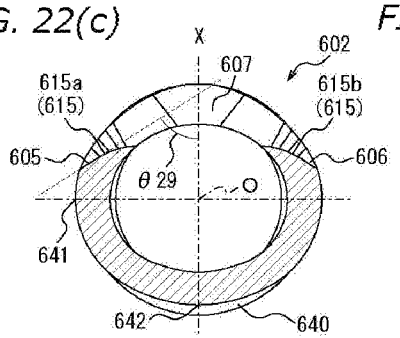
Figure 22D:
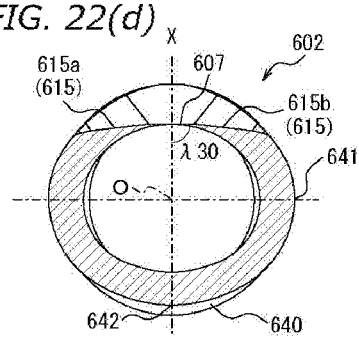
Figure 22E:
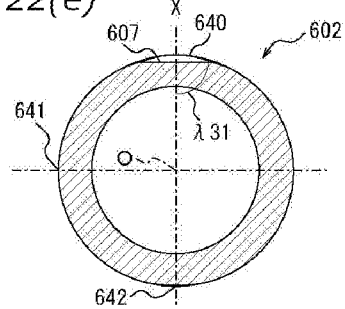

FIGS. 22(a), 22(b), 22(c), 22(d) and 22(e) are cross-sectional views taken along a line XXVII-XXVII, a line XXVIII-XXVIII, a line XXIX-XXIX, a line XXX-XXX and a line XXXI-XXXI of FIG. 21(a), respectively. In the cross-sectional views illustrated in FIGS. 22(a) to 22(e), the angles θ27 to θ29 of the first blade surface portion 605 and the second blade surface portion 606 with respect to the central plane X are equal angles, and the angles λ30 and λ31 of the third blade surface portion 607 with respect to the central plane X are also equal angles at about 90 degrees. As illustrated in FIGS. 22(c) and 22(d), the first blade surface portion 605 and the third blade surface portion 607 are smoothly connected to each other by the four first connecting blade surface portions 615a so as not to form a ridge line that becomes a large step. Likewise, the second blade surface portion 606 and the third blade surface portion 607 are smoothly connected to each other by the four second connecting blade surface portions 615b so as not to form a ridge line that becomes a large step. In FIGS. 22(a) to 22(e), the ridge line between the blade surface portions is indicated by a solid line.

In the puncture needle 601 illustrated in FIGS. 20(a) to 22(e), the blade surface 604 is formed at the distal end portion 603 and is not formed on the needle stem portion 640, but the present invention is not limited to this configuration, and a blade surface may be formed from the distal end portion to the stem portion.

Further, although the first connecting blade surface portion 615a and the second connecting blade surface portion 615b of the puncture needle 601 illustrated in FIGS. 20(a) to 22(e) are each made up of planar blade surface portions, they may be configured by curved blade surface portions.

The medical puncture needle and the method for manufacturing the medical puncture needle according to the present invention are not limited to the specific configurations and methods described in the aforementioned embodiments, but application of the configuration of a part of each of the aforementioned puncture needles to the configuration of another puncture needle to constitute a new puncture needle is within the technical scope of the present invention.

Furthermore, the medical puncture needle and the method for manufacturing the medical puncture needle according to the present invention are not limited to the above-mentioned embodiments, and can be changed within a scope that does not depart from the gist of the invention described in the claims.

INDUSTRIAL APPLICABILITY

The present invention relates to a medical puncture needle and a method for manufacturing a puncture needle.

REFERENCE SIGNS LIST 1, 101, 201, 301, 401, 501, 601: puncture needle
2, 102, 202, 302, 402, 502, 602: main body portion
3, 103, 303, 403, 503, 603: distal end portion of main body portion
4, 104, 204, 304, 404, 504, 604: blade surface
5, 105, 305, 405, 505, 605: first blade surface portion
6, 106, 306, 406, 506, 606: second blade surface portion
7, 107, 307, 407, 507, 607: third blade surface portion
8, 108, 308, 408, 508, 608: needle tip
9, 109, 309, 409, 509, 609: blade edge
10, 110, 310, 510, 610: hollow portion
11, 111, 311, 511, 611: distal end opening
13a, 513a, 613a: first curved portion
13b, 513b, 613b: second curved portion
15, 115, 115, 315, 415, 515, 615: connecting blade surface portion
15a, 115a, 115a', 315a, 415a, 515a, 615a: first connecting blade surface portion
15b, 115b, 115b', 315b, 415b, 515b, 615b: second connecting blade surface portion
16: first ridge portion
17: second ridge portion
18: third ridge portion
19: fourth ridge portion
20: fifth ridge portion
21: sixth ridge portion
60: original shape blade surface portion
70: tubular member
318, 321: ridge portion
422: central ridge portion
423: first ridge portion
424: second ridge portion
425: third ridge portion
426: fourth ridge portion
427: fifth ridge portion
428: sixth ridge portion
429: seventh ridge portion
430: eight ridge portion
502a: distal end side main body portion
502b: proximal end side main body portion
502c: connecting portion
640: needle stem portion
641: tapered portion
642: back inclined portion
A: central axis direction
B: direction orthogonal to central axis
C1: major axis direction
C2: minor axis direction
D1: imaginary straight line passing through point on outer edge of first or second blade surface portion and needle tip in front view
D2: virtual straight line orthogonal to central axis direction passing through proximal end of blade edge in front view
E1: first virtual plane
E2: second virtual plane
E3: third virtual plane
G: grinding surface of tubular member
H: middle position of blade surface region
K: point serving as proximal end of blade surface in side view
L: imaginary straight line passing through needle tip and point serving as proximal end of blade surface in side view
M: proximal end of blade edge
N: point on outer edge of first or second blade surface portion
O: central axis of main body portion
P: central axis of tubular member
Q: boundary line between distal end portion and needle stem portion
R1: proximal end of inner edge of blade surface
R2: proximal end of blade surface
S1: width of distal end side main body portion in plan view
S2: width of distal end side main body portion in side view
S3: width in major axis direction of distal end portion
S4: width in minor axis direction of distal end portion
S5: outer diameter of needle stem portion
T: blade surface region
U: extension line of ridge portion
V: middle position of inner edge of blade surface
W: extension line of third blade surface portion in side view
X: central plane
Y: central axis direction of tubular member
Z: blade surface angle
α: blade tip angle β: cutting edge angle γ1: apparent angle formed by outer edge of first blade surface portion and needle tip in front view γ2: apparent angle formed by outer edge of second blade surface portion and needle tip in front view θ: angle of first and second blade surface portions with respect to central plane in cross section orthogonal to central axis direction δa: angle of first and second connecting blade surface portions on distal end side with respect to central plane in cross section orthogonal to central axis direction δb: angle of first and second connecting blade surface portions on proximal end side with respect to central plane in cross section orthogonal to central axis direction λ: angle of third blade surface portion with respect to central plane in cross section orthogonal to central axis direction ρ1: angle of ridge portion with respect to central axis line in front view ρ2: angle of imaginary straight line passing through point on outer edge of first or second blade surface portion and needle tip with respect to central axis in front view

What is claimed is:

1. A medical puncture needle comprising:
a rod-shaped main body portion; and
a blade surface formed at a distal end portion of the main body portion, wherein the blade surface comprises:
   a first blade surface portion, and a second blade surface portion that intersect to form a blade edge, wherein a needle tip is formed at a location at which a distal end of the blade edge intersects a first ridge line at an outer edge of the first blade surface portion and a second ridge line at an outer edge of the second blade surface portion, and wherein at least one blade surface portion among the first blade surface portion and the second blade surface portion is planar, and, in a central axis direction of the main body portion, said at least one blade surface portion extends to a location proximal of a middle position of the blade surface,
   a third blade surface portion that forms a proximal portion of the blade surface, and
   a plurality of planar connecting blade surface portions located between said at least one blade surface portion and the third blade surface portion, wherein each connecting blade surface portion is continuous with an adjacent connecting blade surface portion with a respective ridge line at a boundary therebetween.

2. The medical puncture needle according to claim 1, wherein a third ridge line at which the third blade surface portion and a first connecting blade surface portion on a proximal end side among the plurality of connecting blade surface portions intersect with each other extends along the central axis direction.

3. The medical puncture needle according to claim 2, wherein:
the main body portion defines a channel that has a distal end opening defined by an inner edge of the blade surface at one end, and
a proximal end of the third ridge line is located between a proximal end of the inner edge of the blade surface and a proximal end of the blade surface, in the central axis direction.

4. The medical puncture needle according to claim 1, wherein, in a side view in which the needle tip is located at one end in a direction orthogonal to the central axis direction, a straight line passing through the needle tip and a proximal end of the blade surface is inclined with respect to the central axis direction at an angle of 13 degrees or more and 20 degrees or less.

5. The medical puncture needle according to claim 1, wherein each of the first blade surface portion and the second blade surface portion is planar, and the first blade surface portion and the second blade surface portion extend to locations proximal of the middle position of the blade surface region.

* * * * *